United States Patent
Ahmadi

(10) Patent No.: US 11,147,973 B2
(45) Date of Patent: Oct. 19, 2021

(54) CHARGE-BALANCED CURRENT-CONTROLLED STIMULATION

(71) Applicant: Mohammad Mahdi Ahmadi, Tehran (IR)

(72) Inventor: Mohammad Mahdi Ahmadi, Tehran (IR)

(73) Assignees: AMIRKABIR UNIVERSITY OF TECHNOLOGY, Tehran (IR); Mohammad Mahdi Ahmadi, Tehran (IR)

(*) Notice: Subject to any disclaimer, the term of this patent is extended or adjusted under 35 U.S.C. 154(b) by 0 days.

(21) Appl. No.: 16/842,077

(22) Filed: Apr. 7, 2020

(65) Prior Publication Data

US 2020/0230418 A1    Jul. 23, 2020

Related U.S. Application Data

(60) Provisional application No. 62/830,459, filed on Apr. 7, 2019.

(51) Int. Cl.
| | |
|---|---|
| *A61N 1/36* | (2006.01) |
| *G11C 7/06* | (2006.01) |
| *H03K 5/24* | (2006.01) |
| *G01R 19/165* | (2006.01) |
| *G11C 27/02* | (2006.01) |

(52) U.S. Cl.
CPC ....... *A61N 1/36125* (2013.01); *A61N 1/3606* (2013.01); *A61N 1/36157* (2013.01); *G01R 19/165* (2013.01); *G11C 7/065* (2013.01); *G11C 27/026* (2013.01); *H03K 5/2481* (2013.01)

(58) Field of Classification Search
CPC ............ A61N 1/36125; A61N 1/36157; A61N 1/3606; G11C 7/065; G11C 27/02; G11C 27/026; G11C 27/024; G11C 27/028; H03K 5/2418; H03K 5/2445; H03K 5/2481; G01R 19/16566; G01R 19/165
See application file for complete search history.

(56) References Cited

U.S. PATENT DOCUMENTS 7,459,967 B2 * 12/2008 Tsuchi ................ H03F 3/45183
330/253

* cited by examiner

*Primary Examiner* — Jung Kim
(74) *Attorney, Agent, or Firm* — Bajwa IP Law Firm; Haris Zaheer Bajwa

(57) ABSTRACT

A circuit for charge-balanced current-controlled stimulation. The circuit includes a transistor differential pair, a first current mirror, a second current mirror, and a third current mirror. The transistor differential pair includes a first differential input node, a second differential input node, a first differential output node, a second differential output node, and a common node. The transistor differential pair is configured to generate a first differential current that passes through the first differential output node and a second differential current that passes through the second differential output node. The first current mirror is configured to generate a first mirrored current based on the first differential current. The second current mirror is configured to generate a second mirrored current based on the second differential current. The third current mirror is configured to generate a third mirrored current based on the first mirrored current.

20 Claims, 11 Drawing Sheets

CHARGE-BALANCED CURRENT-CONTROLLED STIMULATION

CROSS-REFERENCE TO RELATED APPLICATION

This application claims the benefit of priority from U.S. Provisional Patent Application Ser. No. 62/830,459, filed on Apr. 7, 2019, and entitled "CHARGE-BALANCED CURRENT-CONTROLLED STIMULATION CIRCUIT AND METHOD OF OPERATING SAME," which is incorporated herein by reference in its entirety.

TECHNICAL FIELD

The present disclosure generally relates to electrical stimulation, and particularly, to current-controlled stimulation circuits.

BACKGROUND

Electrical stimulation is widely used in many implantable medical devices, such as artificial pacemakers for heartrate management, cochlear implants for treatment of deaf people, spinal cord stimulators for pain management, deep brain stimulators for treatment of Parkinson's disease, and visual prostheses for the treatment of blinds.

Electrical stimulation may be performed by injecting sufficient amount of electrical charge into an excitable tissue. A charge injection may be done by applying a voltage pulse or a current pulse between two electrodes that are placed in the proximity of the tissue. However, any charge accumulation inside the tissue should be avoided as it may cause irreversible Faradaic reactions. Direct current (DC) flowing through the tissue and the stimulation electrodes may cause damage to the tissue.

Several approaches have been proposed to control an amount of electric charge that is injected into a tissue during electrical stimulation. However, due to design mismatches between different elements of electrical stimulators, conventional approaches require complicated circuits to control an exact amount of current that is injected into tissues during electrical stimulation.

There is, therefore, a need for a simple and efficient circuit configuration for electrical stimulation that may facilitate controlling an amount of electric current injected into a tissue during electrical stimulation. There is further a need for a circuit configuration that may minimize the impact of design mismatch on circuit performance.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary circuit for charge-balanced current-controlled stimulation. An exemplary circuit may include a transistor differential pair, a current source, a first current mirror, a second current mirror, a third current mirror, a connecting switch, a first sample and hold circuit, and a second sample and hold circuit.

An exemplary transistor differential pair may include one of a cascode differential pair or a gain-boosted cascode differential pair. In an exemplary embodiment, each of the first current mirror, the second current mirror, and the third current mirror may include one of a cascode current mirror, a regulated cascode current mirror, an enhanced output impedance current mirror, a source-degenerated current mirror, a Widlar current mirror, or a Wilson current mirror.

An exemplary transistor differential pair may include a first transistor, a second transistor, a first differential input node, a second differential input node, a first differential output node, a second differential output node, and a common node. An exemplary transistor differential pair may be configured to generate a first differential current that may pass through the first differential output node and a second differential current that may pass through the second differential output node. In an exemplary embodiment, a difference between the first differential current and the second differential current may be proportional to a voltage difference between the first differential input node and the second differential input node. In an exemplary embodiment, the current source may be configured to generate a source current that may flow through the common node. In an exemplary embodiment, the current source may include a current digital to analog converter (I-DAC). An exemplary I-DAC may be configured to adjust the source current by converting a digital signal to an analog electric current.

An exemplary first current mirror may include a first input current node, a first output current node, and a first supply node. An exemplary first input current node may be connected to the first differential output node. An exemplary first supply node may be coupled with a first supply voltage. In an exemplary embodiment, the first current mirror may be configured to generate a first mirrored current based on the first differential current. An exemplary first mirrored current may flow through the first output current node.

An exemplary second current mirror may include a second input current node, a second output current node, and a second supply node. An exemplary second input current node may be connected to the second differential output node. An exemplary second output current node may be coupled with an output node. An exemplary second supply node may be coupled with the first supply voltage. In an exemplary embodiment, the second current mirror may be configured to generate a second mirrored current based on the second differential current. An exemplary second mirrored current may flow through the second output current node.

An exemplary third current mirror may include a third input current node, a third output current node, and a third supply node. An exemplary third input current node may be connected to the first output current node. An exemplary third supply node may be connected to a second supply voltage. In an exemplary embodiment, the third current mirror may be configured to generate a third mirrored current based on the first mirrored current. An exemplary third mirrored current may flow through the third output current node. In an exemplary embodiment, the connecting switch may be configured to couple the output node with the third output current node responsive to the connecting switch turned on.

An exemplary first sample and hold circuit may include a first sampling switch and a first holding capacitor. In an exemplary embodiment, the first sample and hold circuit may be configured to sample an output voltage at the output node responsive to the first sampling switch turned on and hold the output voltage at the first differential input node utilizing the first holding capacitor responsive to the first sampling switch turned off.

An exemplary second sample and hold circuit may include a second sampling switch and a second holding capacitor. In an exemplary embodiment, the second sample and hold circuit may be configured to sample a reference voltage applied to a reference node responsive to the second sampling switch turned on and hold the reference voltage at the second differential input node utilizing the second holding capacitor responsive to the second sampling switch turned off.

In an exemplary embodiment, the first holding capacitor may be connected between the first differential input node and a ground node and the first sampling switch may be connected between the first differential input node and the output node. In an exemplary embodiment, the second holding capacitor may be connected between the second differential input node and the ground node and the second sampling switch may be connected between the second differential input node and the reference node.

In an exemplary embodiment, the first transistor may include a first field effect transistor (FET) of a first plurality of FETs. An exemplary first FET may include a first source, a first gate, and a first drain. An exemplary first source may be connected to the common node. An exemplary first gate may be connected to the first differential input node. An exemplary first drain may be connected to the first differential output node.

In an exemplary embodiment, the second transistor may include a second FET of the first plurality of FETs. An exemplary second FET may include a second source, a second gate, and a second drain. An exemplary second source may be connected to the common node. An exemplary second gate may be connected to the second differential input node. An exemplary second drain may be connected to the second differential output node.

In an exemplary embodiment, the first current mirror may further include a third FET of a second plurality of FETs. An exemplary third FET may include a third source, a third gate, and a third drain. An exemplary third source may be coupled with the first supply node. An exemplary third gate may be coupled with the first input current node. An exemplary third drain may be coupled with the first input current node.

In an exemplary embodiment, the first current mirror may further include a fourth FET of the second plurality of FETs. An exemplary fourth FET may include a fourth source, a fourth gate, and a fourth drain. An exemplary fourth source may be coupled with the first supply node. An exemplary fourth gate may be coupled with the third gate. An exemplary fourth drain may be coupled with the first output current node.

In an exemplary embodiment, the second current mirror may further include a fifth FET of the second plurality of FETs. An exemplary fifth FET may include a fifth source, a fifth gate, and a fifth drain. An exemplary fifth source may be coupled with the second supply node.

An exemplary fifth gate may be coupled with the second input current node. An exemplary fifth drain may be coupled with the second input current node.

In an exemplary embodiment, the second current mirror may further include a sixth FET of the second plurality of FETs. An exemplary sixth FET may include a sixth source, a sixth gate, and a sixth drain. An exemplary sixth source may be coupled with the second supply node. An exemplary sixth gate may be coupled with the fifth gate. An exemplary sixth drain may be coupled with the second output current node.

In an exemplary embodiment, the third current mirror may further include a seventh FET of the first plurality of FETs. An exemplary seventh FET may include a seventh source, a seventh gate, and a seventh drain. An exemplary seventh source may be connected to the third supply node. An exemplary seventh gate coupled with the third input current node. An exemplary seventh drain may be coupled with the third input current node.

In an exemplary embodiment, the third current mirror may further include an eighth FET of the first plurality of FETs. An exemplary eighth FET may include an eighth source, an eighth gate, and an eighth drain. An exemplary eighth source may be connected to the third supply node. An exemplary eighth gate may be connected to the seventh gate. An exemplary eighth drain may be coupled with the third output current node.

In an exemplary embodiment, each of the first plurality of FETs may include a first type of FETs and each of the second plurality of FETs may include a second type of FETs. An exemplary second type of FETs may be different from the first type. In an exemplary embodiment, each of the first type and the second type may include alternatively one of n-channel FETs or a p-channel FETs.

In an exemplary embodiment, the first current mirror may further include a ninth FET of the second plurality of FETs. An exemplary ninth FET may be connected between the first input current node and the third drain. An exemplary ninth FET may include a ninth source, a ninth gate, and a ninth drain. An exemplary ninth source may be connected to the third drain. An exemplary ninth gate may be connected to the first input current node. An exemplary ninth drain may be connected to the first input current node.

In an exemplary embodiment, the first current mirror may further include a tenth FET of the second plurality of FETs. An exemplary tenth FET may be connected between the first output current node and the fourth drain. An exemplary tenth FET may include a tenth source, a tenth gate, and a tenth drain. An exemplary tenth source may be connected to the fourth drain. An exemplary tenth gate may be connected to the ninth gate. An exemplary tenth drain may be connected to the first output current node.

In an exemplary embodiment, the second current mirror may further include an eleventh FET of the second plurality of FETs. An exemplary eleventh FET may be connected between the second input current node and the fifth drain. An exemplary eleventh FET may include an eleventh source, an eleventh gate, and an eleventh drain. An exemplary eleventh source may be connected to the fifth drain. An exemplary eleventh gate may be connected to the second input current node. An exemplary eleventh drain connected to the second input current node.

In an exemplary embodiment, the second current mirror may further include a twelfth FET of the second plurality of FETs. An exemplary twelfth FET may be connected between the second output current node and the sixth drain. An exemplary twelfth FET may include a twelfth source, a twelfth gate, and a twelfth drain. An exemplary twelfth source may be connected to the sixth drain. An exemplary twelfth gate may be connected to the eleventh gate. An exemplary twelfth drain may be connected to the second output current node.

In an exemplary embodiment, the third current mirror may further include a thirteenth FET of the first plurality of FETs. An exemplary thirteenth FET may be connected between the third input current node and the seventh drain. An exemplary thirteenth FET may include a thirteenth source, a thirteenth gate, and a thirteenth drain. An exemplary thirteenth source may be connected to the seventh drain. An exemplary thirteenth gate may be connected to the third input current node. An exemplary thirteenth drain may be connected to the third input current node.

In an exemplary embodiment, the third current mirror may further include a fourteenth FET of the first plurality of FETs. An exemplary fourteenth FET may be connected between the third output current node and the eighth drain. An exemplary fourteenth FET may include a fourteenth source, a fourteenth gate, and a fourteenth drain. An exemplary fourteenth source may be connected to the eighth drain. An exemplary fourteenth gate may be connected to the thirteenth gate. An exemplary fourteenth drain may be connected to the third output current node.

An exemplary circuit may further include a first voltage buffer and a second voltage buffer. An exemplary first voltage buffer may be connected between the output node and the first sample and hold circuit. In an exemplary embodiment, the first voltage buffer may be configured to transfer the output voltage to the first sample and hold circuit. An exemplary second voltage buffer may be connected between the reference node and the second sample and hold circuit. In an exemplary embodiment, the second voltage buffer may be configured to transfer the reference voltage to the second sample and hold circuit.

In an exemplary embodiment, the first current mirror may further include a fifteenth FET of the second plurality of FETs connected between the first input current node and the third drain. In an exemplary embodiment, the fifteenth FET may include a fifteenth source connected to the third drain, a fifteenth gate, and a fifteenth drain connected to the third gate.

In an exemplary embodiment, the first current mirror may further include a sixteenth FET of the second plurality of FETs connected between the first output current node and the fourth drain. In an exemplary embodiment, the sixteenth FET may include a sixteenth source connected to the fourth drain, a sixteenth gate connected to the fifteenth gate, and a sixteenth drain connected to the first output current node.

In an exemplary embodiment, the first current mirror may further include a seventeenth FET of the second plurality of FETs connected between the first input current node and the fifteenth drain. In an exemplary embodiment, the seventeenth FET may include a seventeenth source connected to the fifteenth drain, a seventeenth gate connected to the first input current node, and a seventeenth drain connected to the fifteenth gate.

In an exemplary embodiment, the first current mirror may further include an eighteenth FET of the second plurality of FETs connected between the first input current node and the seventeenth drain. In an exemplary embodiment, the eighteenth FET may include an eighteenth source connected to the seventeenth drain, an eighteenth gate connected to the first input current node, and an eighteenth drain connected to the first input current node.

In an exemplary embodiment, the second current mirror may further include a nineteenth FET of the second plurality of FETs connected between the second input current node and the fifth drain. In an exemplary embodiment, the nineteenth FET may include a nineteenth source connected to the fifth drain, a nineteenth gate, and a nineteenth drain connected to the fifth gate.

In an exemplary embodiment, the second current mirror may further include a twentieth FET of the second plurality of FETs connected between the second output current node and the sixth drain. In an exemplary embodiment, the twentieth FET may include a twentieth source connected to the sixth drain, a twentieth gate connected to the nineteenth gate, and a twentieth drain connected to the second output current node.

In an exemplary embodiment, the second current mirror may further include a twenty-first FET of the second plurality of FETs connected between the second input current node and the nineteenth drain. In an exemplary embodiment, the twenty-first FET may include a twenty-first source connected to the nineteenth drain, a twenty-first gate connected to the second input current node, and a twenty-first drain connected to the nineteenth gate.

In an exemplary embodiment, the second current mirror may further include a twenty-second FET of the second plurality of FETs connected between the second input current node and the twenty-first drain. In an exemplary embodiment, the twenty-second FET may include a twenty-second source connected to the twenty-first drain, a twenty-second gate connected to the second input current node, and a twenty-second drain connected to the second input current node.

In an exemplary embodiment, the third current mirror may further include a twenty-third FET of the first plurality of FETs connected between the third input current node and the seventh drain. In an exemplary embodiment, the twenty-third FET may include a twenty-third source connected to the seventh drain, a twenty-third gate, and a twenty-third drain connected to the seventh gate.

In an exemplary embodiment, the third current mirror may further include a twenty-fourth FET of the first plurality of FETs connected between the third output current node and the eighth drain. In an exemplary embodiment, the twenty-fourth FET may include a twenty-fourth source connected to the eighth drain, a twenty-fourth gate connected to the twenty-third gate, and a twenty-fourth drain connected to the third output current node.

In an exemplary embodiment, the third current mirror may further include a twenty-fifth FET of the first plurality of FETs connected between the third input current node and the twenty-third drain. In an exemplary embodiment, the twenty-fifth FET may include a twenty-fifth source connected to the twenty-third drain, a twenty-fifth gate connected to the third input current node, and a twenty-fifth drain connected to the twenty-third gate.

In an exemplary embodiment, the third current mirror may further include a twenty-sixth FET of the first plurality of FETs connected between the third input current node and the twenty-fifth drain. In an exemplary embodiment, the twenty-sixth FET may include a twenty-sixth source connected to the twenty-fifth drain, a twenty-sixth gate connected to the third input current node, and a twenty-sixth drain connected to the third input current node.

In an exemplary embodiment, the first current mirror may further include a twenty-seventh FET of the second plurality of FETs connected between the first input current node and the third drain. In an exemplary embodiment, the twenty-seventh FET may include a twenty-seventh source connected to the third drain, a twenty-seventh gate, and a twenty-seventh drain connected to the third gate.

In an exemplary embodiment, the first current mirror may further include a twenty-eighth FET of the second plurality of FETs connected between the first output current node and the fourth drain. In an exemplary embodiment, the twenty-eighth FET may include a twenty-eighth source connected to the fourth drain, a twenty-eighth gate connected to the twenty-seventh gate, and a twenty-eighth drain connected to the first output current node.

In an exemplary embodiment, the first current mirror may further include a twenty-ninth FET of the second plurality of FETs. An exemplary twenty-ninth FET may include a twenty-ninth source connected to the first supply node, a twenty-ninth gate connected to the twenty-eighth gate, and a twenty-ninth drain connected to the twenty-ninth gate.

In an exemplary embodiment, the first current mirror may further include a thirtieth FET of the second plurality of FETs. An exemplary thirtieth FET may include a thirtieth source connected to the first supply node, a thirtieth gate coupled with the third gate, and a thirtieth drain. In an exemplary embodiment, the first current mirror may further include a first resistor connected between the thirtieth gate and the third gate.

In an exemplary embodiment, the second current mirror may further include a thirty-first FET of the second plurality of FETs connected between the second input current node and the fifth drain. In an exemplary embodiment, the thirty-first FET may include a thirty-first source connected to the fifth drain, a thirty-first gate connected to the twenty-seventh gate, and a thirty-first drain connected to the fifth gate.

In an exemplary embodiment, the second current mirror may further include a thirty-second FET of the second plurality of FETs connected between the second output current node and the sixth drain. In an exemplary embodiment, the thirty-second FET may include a thirty-second source connected to the sixth drain, a thirty-second gate coupled with the thirty-first gate, and a thirty-second drain connected to the second output current node. In an exemplary embodiment, the second current mirror may further include a second resistor connected between the fifth gate and the first resistor.

In an exemplary embodiment, the third current mirror may further include a thirty-third FET of the first plurality of FETs connected between the third input current node and the seventh drain. In an exemplary embodiment, the thirty-third FET may include a thirty-third source connected to the seventh drain, a thirty-third gate, and a thirty-third drain connected to the seventh gate.

In an exemplary embodiment, the third current mirror may further include a thirty-fourth FET of the first plurality of FETs connected between the third output current node and the eighth drain. In an exemplary embodiment, the thirty-fourth FET may include a thirty-fourth source connected to the eighth drain, a thirty-fourth gate coupled with the thirty-third gate, and a thirty-fourth drain connected to the third output current node.

In an exemplary embodiment, the third current mirror may further include a thirty-fifth FET of the first plurality of FETs. An exemplary thirty-fifth FET may include a thirty-fifth source connected to the third supply node, a thirty-fifth gate connected to the thirty-third gate, and a thirty-fifth drain connected to the twenty-ninth drain.

In an exemplary embodiment, the third current mirror may further include a thirty-sixth FET of the first plurality of FETs. An exemplary thirty-sixth FET may include a thirty-sixth source connected to the third supply node, a thirty-sixth gate connected to the thirty-fifth gate, and a thirty-sixth drain connected to the thirtieth drain and the thirty-sixth gate.

An exemplary circuit may further include a first operational amplifier (op-amp) configured to couple the thirty-first FET with the thirty-second FET. In an exemplary embodiment, the first op-amp may include a first inverting input connected to the thirty-second source, a first non-inverting input connected to the thirty-first source, and a first op-amp output connected to the thirty-second gate.

An exemplary circuit may further include a second op-amp configured to couple the thirty-third FET with the thirty-fourth FET. In an exemplary embodiment, the second op-amp may include a second inverting input connected to the thirty-fourth source, a second non-inverting input connected to the thirty-third source, and a second op-amp output connected to the thirty-fourth gate.

An exemplary circuit may further include a supplementary switch and an RC circuit. An exemplary supplementary switch may be connected between the second output current node and the output node. In an exemplary embodiment, the supplementary switch may be configured to connect the second output current node to the output node responsive to the supplementary switch turned on. An exemplary RC circuit may be connected between the output node and the ground node. In an exemplary embodiment, the RC circuit may include a compensating resistor and a compensating capacitor connected in series.

In an exemplary embodiment, the first current mirror may further include a first transfer ratio equal to one. In an exemplary embodiment, the second current mirror may further include a second transfer ratio equal to four. In an exemplary embodiment, the third current mirror may further include a third transfer ratio equal to four.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary current-controlled electrical stimulator. An exemplary current-controlled electrical stimulator may generate a current sink and a current source with substantially matched current amplitudes. An exemplary circuit may include a differential pair whose tail current may be controlled utilizing a digital-to-analog converter. An exemplary current in one side of the differential pair may be mirrored and copied onto a transistor that is generating a current source. An exemplary current in another side of the different pair may be mirrored and copied onto a transistor generating a current sink. An exemplary circuit may incorporate two sample and hold circuits connected to inputs of an exemplary transistor differential pair. Operation cycles of an exemplary circuit may include a sampling phase, during which a feedback may be placed around the circuit making the sink current substantially equal to the source current. After the sampling phase, an exemplary voltage offset that keeps the sink and source currents substantially equal may be sampled on an exemplary sample and hold circuits to provide a stimulation current that may stimulate an object under study.

Figure 1:
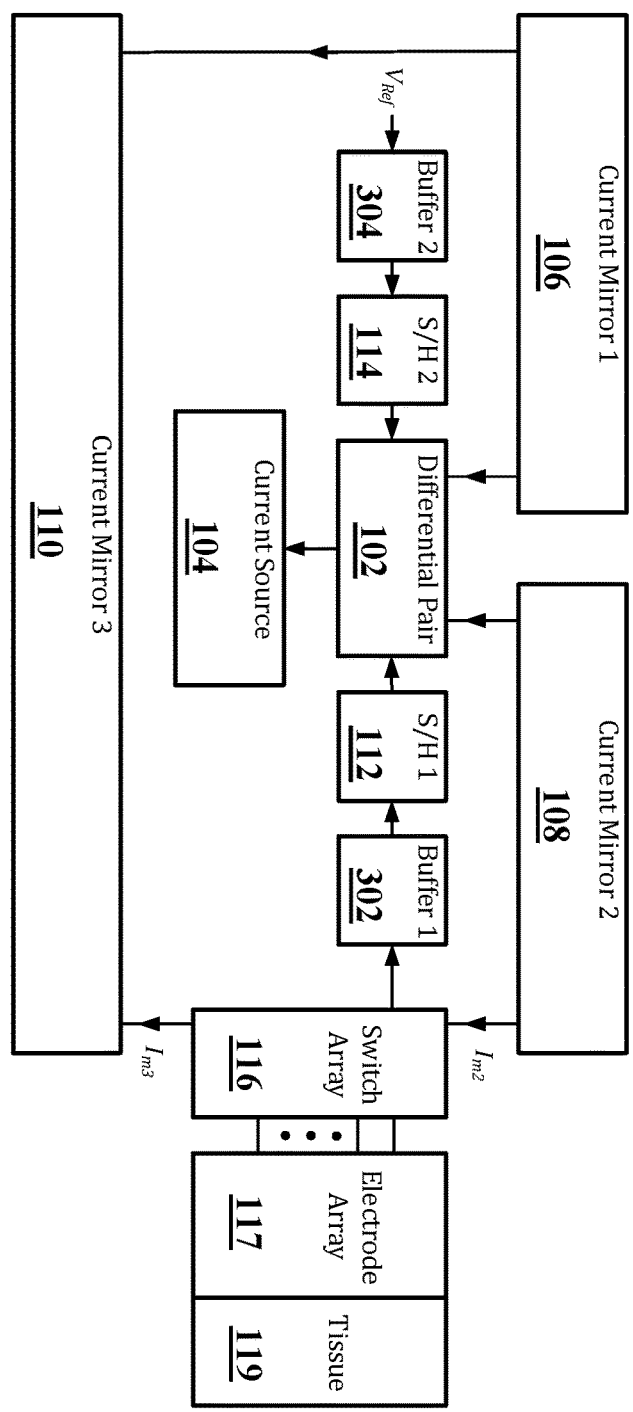
FIG. 1 shows a high-level block diagram of a circuit for charge-balanced current-controlled stimulation, consistent with one or more exemplary embodiments of the present disclosure.

FIG. 1 shows a high-level block diagram of a circuit for charge-balanced current-controlled stimulation, consistent with one or more exemplary embodiments of the present disclosure. An exemplary circuit 100 may include a transistor differential pair 102, a current source 104, a first current mirror 106, a second current mirror 108, a third current mirror 110, a first sample and hold circuit 112, a second sample and hold circuit 114, and a switch array 116.

In an exemplary embodiment, circuit 100 may be utilized to stimulate a tissue 117 via an electrode array 119. An exemplary stimulation process may include generating a stimulation current by equalizing an electric current $I_{m2}$ flowing through second current mirror 108 and an electric current $I_{m3}$ flowing through third current mirror 110 utilizing circuit 100. In an exemplary embodiment, the stimulation current may then be injected into tissue 117 by turning on switch array 116 via electrode array 119, as described below.

In an exemplary embodiment, transistor differential pair 102 may be implemented utilizing different types of differential pairs, such as a cascode differential pair or a gain-boosted cascode differential pair. Moreover, in an exemplary embodiment, each of first current mirror 106, second current mirror 108, and third current mirror 110 may include different implementations of current mirrors, such as a cascode current mirror, a regulated cascode current mirror, an enhanced output impedance current mirror, a source-degenerated current mirror, a Widlar current mirror, or a Wilson current mirror.

Figure 2A:
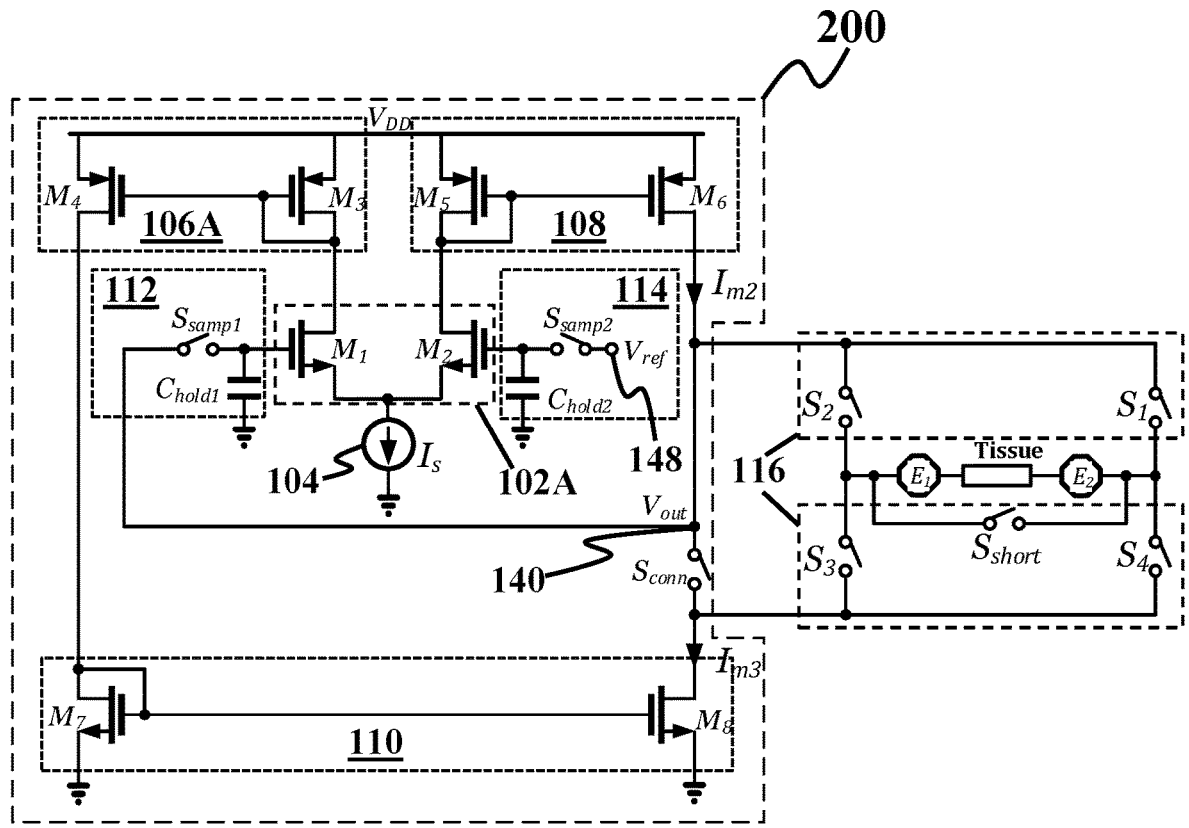
FIG. 2A shows a schematic of a first implementation of a circuit for charge-balanced current-controlled stimulation, consistent with one or more exemplary embodiments of the present disclosure.

FIG. 2A shows a schematic of a first implementation of a circuit for charge-balanced current-controlled stimulation, consistent with one or more exemplary embodiments of the present disclosure. An exemplary circuit 200 may be similar to circuit 100.

Figure 2B:
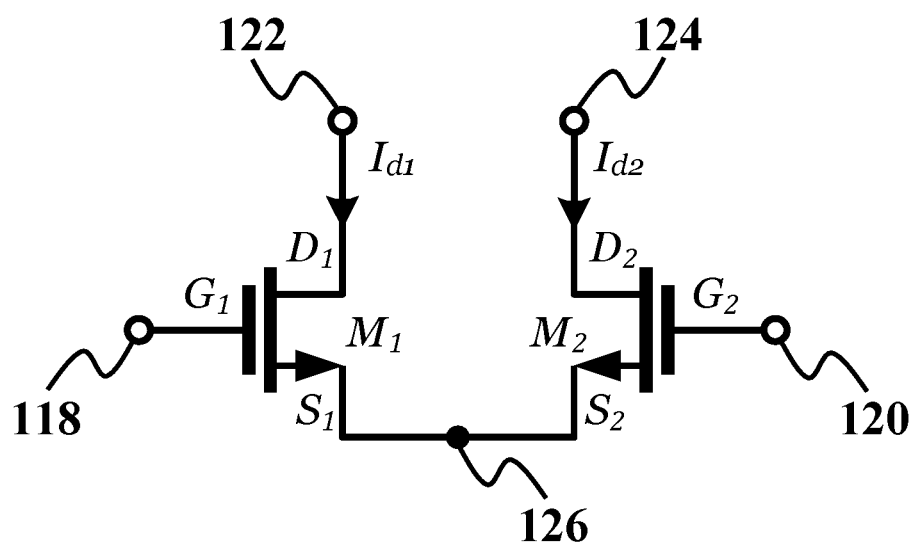
FIG. 2B shows a schematic of a transistor differential pair, consistent with one or more exemplary embodiments of the present disclosure.

FIG. 2B shows a schematic of a transistor differential pair, consistent with one or more exemplary embodiments of the present disclosure. Referring to FIGS. 1, 2A, and 2B, an exemplary transistor differential pair 102A may comprise of an implementation of transistor differential pair 102. In an exemplary embodiment, as shown in FIG. 2B, transistor differential pair 102A may include a first transistor $M_1$, a second transistor $M_2$, a first differential input node 118, a second differential input node 120, a first differential output node 122, a second differential output node 124, and a common node 126. In an exemplary embodiment, transistor differential pair 102A may be configured to generate a first differential current $I_{d1}$ that may pass through first differential output node 122 and a second differential current $I_{d2}$ that may pass through second differential output node 124. In an exemplary embodiment, a difference between first differential current $I_{d1}$ and second differential current $I_{d2}$ may be proportional to a voltage difference between first differential input node 118 and second differential input node 120. In an exemplary embodiment, current source 104 may be configured to generate a source current $I_s$ from that may flow through common node 126. In an exemplary embodiment, first transistor $M_1$ and second transistor $M_2$ may include a pair of matched transistors.

In an exemplary embodiment, first transistor $M_1$ may include a first field effect transistor (FET) of a first plurality of FETs. An exemplary first FET may include a first source $S_1$, a first gate $G_1$, and a first drain $D_1$. In an exemplary embodiment, first source $S_1$ may be connected to common node 126. In an exemplary embodiment, first gate $G_1$ may be connected to first differential input node 118. In an exemplary embodiment first drain $D_1$ may be connected to first differential output node 122.

In an exemplary embodiment, second transistor $M_2$ may include a second FET of the first plurality of FETs. An exemplary second FET may include a second source $S_2$, a second gate $G_2$, and a second drain $D_2$. An exemplary second source $S_2$ may be connected to common node 126. In an exemplary embodiment, second gate $G_2$ may be connected to second differential input node 120. In an exemplary embodiment, second drain $D_2$ may be connected to second differential output node 124.

Figure 2C:
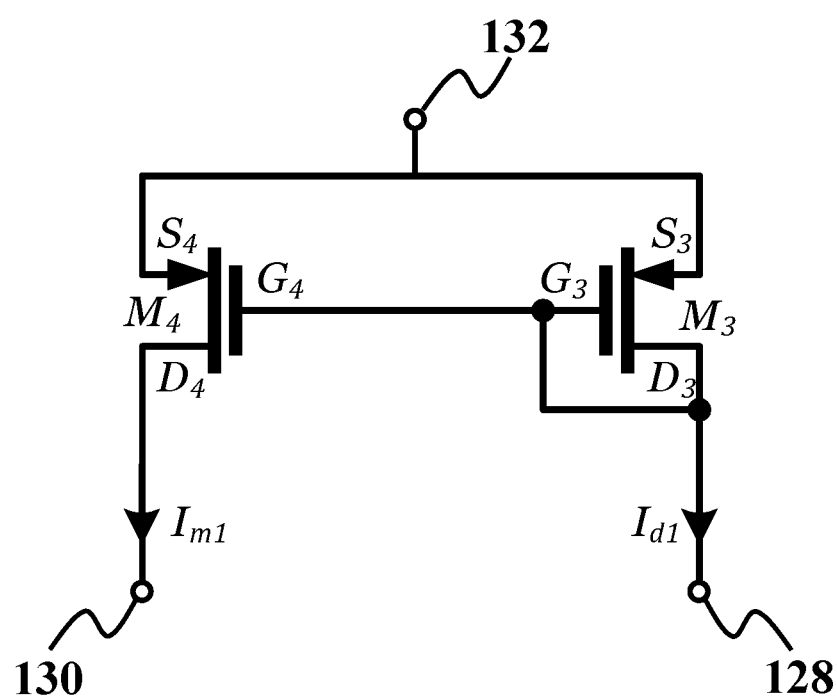
FIG. 2C shows a schematic of a first implementation of a first current mirror, consistent with one or more exemplary embodiments of the present disclosure.

FIG. 2C shows a schematic of a first implementation of a first current mirror, consistent with one or more exemplary embodiments of the present disclosure. Referring to FIGS. 1, 2A, and 2C, an exemplary first current mirror 106A may be a first implementation of first current mirror 106. In an exemplary embodiment, first current mirror 106A may include a first input current node 128, a first output current node 130, and a first supply node 132. In an exemplary embodiment, first input current node 130 may be connected to first differential output node 122. In an exemplary embodiment, first supply node 132 may be coupled with a first supply voltage $V_{DD}$. In an exemplary embodiment, first current mirror 106A may be configured to generate a first mirrored current $I_{m1}$ based on first differential current $I_{d1}$. In an exemplary embodiment, first mirrored current $I_{m1}$ may flow through first output current node 130.

In an exemplary embodiment, first current mirror 106A may further include a third FET $M_3$ of a second plurality of FETs. In an exemplary embodiment, third FET $M_3$ may include a third source $S_3$, a third gate $G_3$, and a third drain $D_3$. In an exemplary embodiment, third source $S_3$ may be coupled with first supply node 132. In an exemplary embodiment, third drain $D_3$ and third gate $G_3$ may be coupled with first input current node 128.

In an exemplary embodiment, first current mirror 106A may further include a fourth FET $M_4$ of the second plurality of FETs. In an exemplary embodiment, fourth FET $M_4$ may include a fourth source $S_4$, a fourth gate $G_4$, and a fourth drain $D_4$. In an exemplary embodiment, fourth source $S_4$ may be coupled with first supply node 132. In an exemplary embodiment, fourth gate $G_4$ may be coupled with third gate $G_1$. In an exemplary embodiment, fourth drain $D_4$ may be coupled with first output current node 130.

Figure 2D:
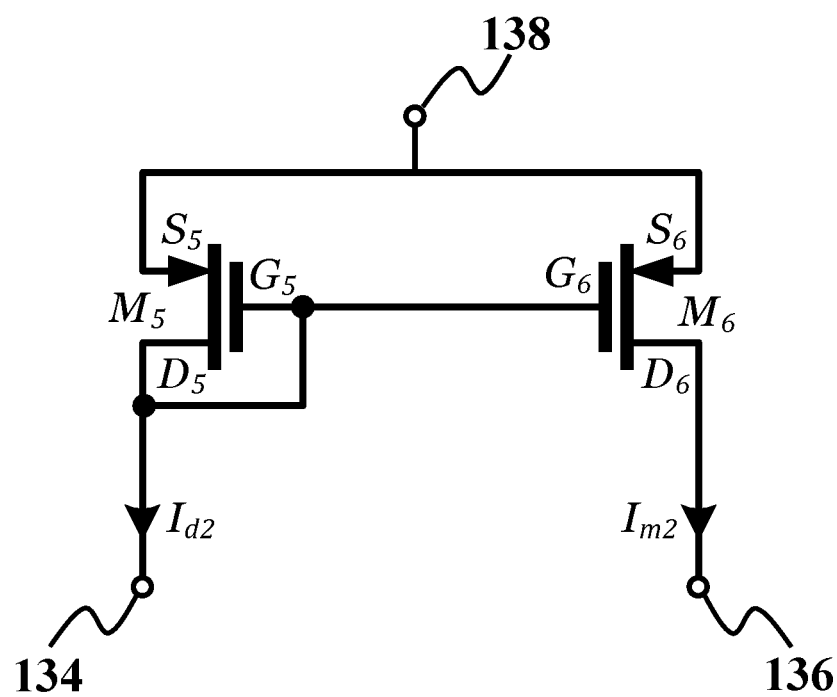
FIG. 2D shows a schematic of a first implementation of a second current mirror, consistent with one or more exemplary embodiments of the present disclosure.

FIG. 2D shows a schematic of a first implementation of a second current mirror, consistent with one or more exemplary embodiments of the present disclosure. Referring to FIGS. 1, 2A, and 2D, an exemplary second current mirror 108A may be a first implementation of second current mirror 108. In an exemplary embodiment, second current mirror 108A may comprise a second input current node 134, a second output current node 136, and a second supply node 138. In an exemplary embodiment, second input current node 134 may be connected to second differential output node 124. In an exemplary embodiment, second output current node 136 may be coupled with an output node 140. In an exemplary embodiment, second supply node 138 may be coupled with first supply voltage $V_{DD}$. In an exemplary embodiment, second current mirror 108A may be configured to generate a second mirrored current $I_{m2}$ based on second differential current $I_{d2}$. In an exemplary embodiment, second mirrored current $I_{m2}$ may flow through second output current node 136.

In an exemplary embodiment, second current mirror 108A may further include a fifth FET $M_5$ of the second plurality of FETs. In an exemplary embodiment, fifth FET $M_5$ may include a fifth source $S_5$, a fifth gate $G_5$, and a fifth drain $D_5$. In an exemplary embodiment, fifth source $S_5$ may be coupled with second supply node 138. In an exemplary embodiment, fifth gate $G_5$ and fifth drain $D_5$ may be coupled with second input current node 134.

In an exemplary embodiment, second current mirror 108A may further include a sixth FET $M_6$ of the second plurality of FETs. In an exemplary embodiment, sixth FET $M_6$ may include a sixth source $S_6$, a sixth gate $G_6$, and a sixth drain $D_6$. In an exemplary embodiment, sixth source $S_6$ may be coupled with second supply node 138. In an exemplary embodiment, sixth gate $G_6$ may be coupled with fifth gate $G_5$. In an exemplary embodiment, sixth drain $D_6$ may be coupled with second output current node 136.

Figure 2E:
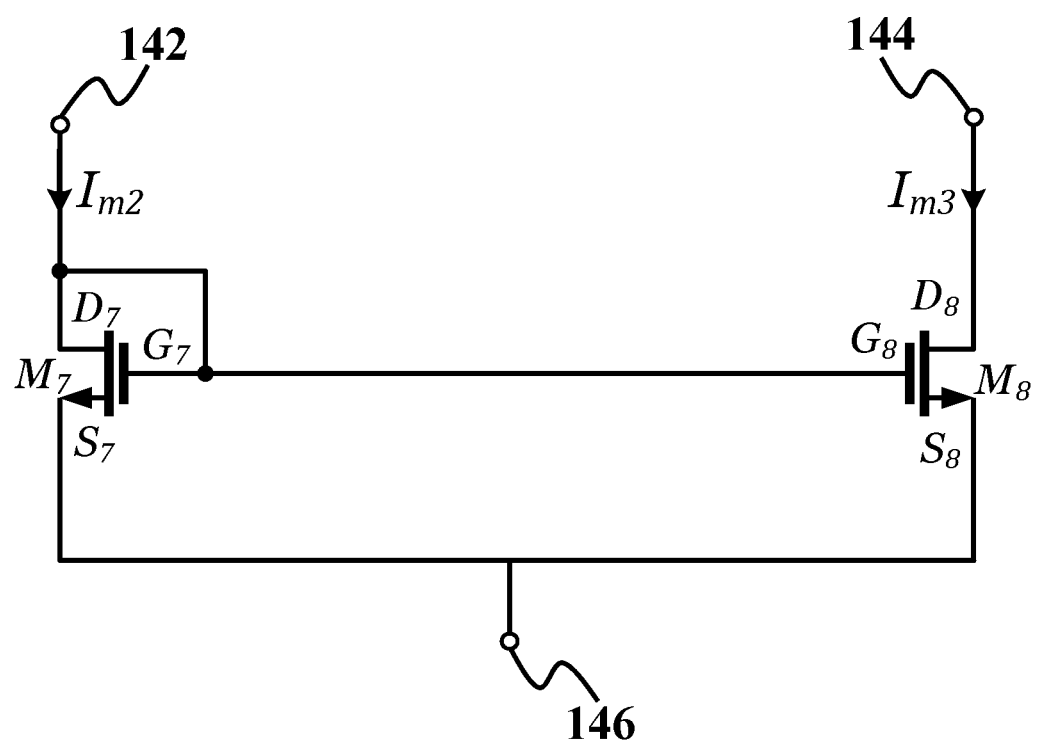
FIG. 2E shows a schematic of a first implementation of a third current mirror, consistent with one or more exemplary embodiments of the present disclosure.

FIG. 2E shows a schematic of a first implementation of a third current mirror, consistent with one or more exemplary embodiments of the present disclosure. Referring to FIGS. 1, 2A, and 2D, an exemplary third current mirror 110A may be a first implementation of third current mirror 110. In an exemplary embodiment, third current mirror 110A may comprise a third input current node 142, a third output current node 144, and a third supply node 146. In an exemplary embodiment, third input current node 1442 may be connected to first output current node 130. In an exemplary embodiment, third supply node 146 may be connected to a second supply voltage. An exemplary second supply voltage may provide different voltage levels, including a voltage level equal to a voltage level at a ground node of circuit 200. In an exemplary embodiment, third current mirror 110A may be configured to generate a third mirrored current $I_{m3}$ based on the first mirrored current. In an exemplary embodiment, third mirrored current $I_{m3}$ may flow through third output current node 144.

In an exemplary embodiment, third current mirror 110A may further include a seventh FET $M_7$ of the first plurality of FETs. In an exemplary embodiment, seventh FET $M_7$ may include a seventh source $S_7$, a seventh gate $G_7$, and a seventh drain $D_7$. In an exemplary embodiment, seventh source $S_7$ may be connected to third supply node 146, in an exemplary embodiment, seventh gate $G_7$ and seventh drain $D_7$ may be coupled with third input current node 142.

In an exemplary embodiment, third current mirror 110A may further include an eighth FET $M_5$ of the first plurality of FETs. In an exemplary embodiment, eighth FET $M_5$ may include an eighth source $S_8$, an eighth gate $G_8$, and an eighth drain $D_8$. In an exemplary embodiment, eighth source $S_8$ may be connected to third supply node 146. In an exemplary embodiment, eighth gate $G_8$ may be connected to seventh gate $G_7$. In an exemplary embodiment, eighth drain $D_8$ may be coupled with third output current node 144.

In an exemplary embodiment, each of the first plurality of FETs may include a first type of FETs and each of the second plurality of FETs may include a second type of FETs. An exemplary second type of FETs may be different from the first type. In an exemplary embodiment, each of the first type and the second type may alternatively be one of n-channel FETs or a p-channel FETs. Therefore, in an exemplary embodiment, if the first plurality of FETs may include n-channel FETs, the second plurality of FETs may include p-channel FETs. In an exemplary embodiment, if the first plurality of FETs may include p-channel FETs, the second plurality of FETs may include n-channel FETs.

Referring again to FIGS. 2A-2E, in an exemplary embodiment, FETs $M_3$ and $M_4$ in first current mirror 106A and FETs $M_5$, and $M_5$ in second current mirror 108 may be matched together in design and layout, i.e., FETs $M_3$-$M_6$ may be designed and fabricated in a same condition. In an exemplary embodiment, FETs $M_7$ and $M_5$ in third current mirror 110A may also be matched in design and layout. In an exemplary embodiment, mirroring ratios in first current mirror 106A, second current mirror 108A, and third current mirror 110A may be 1:1, and therefore currents flowing through transistors in each of the current mirrors may be about half of source current $I_s$. Consequently, a current dissipation of circuit 200 may be about $2 \times I_s$. In order to reduce the current dissipation, in an exemplary embodiment, the ratio in the current mirrors may be modified. For example, if the current-copying ratio changes to 1:10 in second current mirror 108A and third current mirror 110A, the current dissipation of circuit 200 may be reduced to about $0.65 \times I_s$.

In an exemplary embodiment, if a feedback between output node 140 and first differential input node 118 does not exist, second mirrored current $I_{m2}$ flowing through $M_6$ may not be exactly equal to third mirrored current $I_{m3}$ flowing through $M_8$, as the devices may not be precisely matched.

In an exemplary embodiment, first sample and hold circuit 112 may include a first sampling switch $S_{samp1}$ and a first holding capacitor $C_{hold1}$. In an exemplary embodiment, first sample and hold circuit 112 may be configured to sample an output voltage $V_{out}$ at output node 140 responsive to the first sampling switch $S_{samp1}$ turned on and hold output voltage $V_{out}$ at first differential input node 118 utilizing first holding capacitor $C_{hold1}$ responsive to first sampling switch $S_{samp1}$ turned off. In an exemplary embodiment, first holding capacitor $C_{hold1}$ may be connected between first differential input node 118 and a ground node of circuit 200 and first sampling switch $S_{samp1}$ may be connected between first differential input node 118 and output node 140. In an exemplary embodiment, first sampling switch $S_{samp1}$ may be implemented utilizing a single FET or a dual FET switch.

In an exemplary embodiment, second sample and hold circuit 114 may include a second sampling switch $S_{samp2}$ and a second holding capacitor $C_{hold2}$. In an exemplary embodiment, second sample and hold circuit 114 may be configured to sample a reference voltage $V_{ref}$ applied to a reference node 148 responsive to second sampling switch $S_{samp2}$ turned on and hold reference voltage $V_{ref}$ at second differential input node 120 utilizing second holding capacitor $C_{hold2}$ responsive to second sampling switch $S_{samp2}$ turned off. In an exemplary embodiment, second holding capacitor $C_{hold2}$ may be connected between second differential input node 120 and the ground node of circuit 200 and second sampling switch $S_{samp2}$ may be connected between second differential input node 120 and reference node 148. In an exemplary embodiment, second sampling switch $S_{samp2}$ may be implemented utilizing a single FET or a dual FET switch.

In an exemplary embodiment, circuit 200 may further include a connecting switch $S_{conn}$. In an exemplary embodiment, connecting switch $S_{conn}$ may be configured to couple output node 140 with third output current node 144 responsive to connecting switch $S_{conn}$ turned on. In an exemplary embodiment, turning on connecting switch $S_{conn}$ may result in equalizing of first mirrored current $I_{m1}$ and second mirrored current $I_{m2}$. In an exemplary embodiment, in order to stimulate tissue 117, connecting switch $S_{conn}$ may be turned off to let second mirrored current $I_{m2}$ flow through electrode array 119. In an exemplary embodiment, to keep the level of second mirrored current $I_{m2}$ unchanged after starting a tissue stimulation, voltage levels at first differential input node 118 and second differential input node 120 may be kept unchanged before and after starting the stimulation. Therefore, in an exemplary embodiment, first sampling switch $S_{samp1}$ and second sampling switch $S_{samp2}$ may be kept turned on for a first period of time (referred to a sampling phase) that may be determined based on a capacitance of first holding capacitor $C_{hold1}$ and a capacitance of second holding capacitor $C_{hold2}$. In other words, first sampling switch $S_{samp1}$ and second sampling switch $S_{samp2}$ may remain active until first holding capacitor $C_{hold1}$ and second holding capacitor $C_{hold2}$ may become fully charged. Afterwards, in an exemplary embodiment, first sampling switch $S_{samp1}$, second sampling switch $S_{samp2}$, and connecting switch $S_{conn}$ may be turned off to start a stimulation phase by passing a stimulation current through tissue 117. In an exemplary embodiment, first sampling switch $S_{samp1}$ and second sampling switch $S_{samp2}$ may be turned off slightly before turning off connecting switch $S_{conn}$. In an exemplary embodiment, a slight delay in turning off connecting switch $S_{conn}$ may cause the effects of channel charge injection and clock feed through to have a similar impact on first sampling switch $S_{samp1}$ and second sampling switch $S_{samp2}$.

In an exemplary embodiment, the stimulation phase may include a cathodic stimulation and an anodic stimulation. In an exemplary embodiment, during the cathodic stimulation, the stimulation current may be passed through the tissue in a negative direction (i.e., from an anode end $E_2$ of tissue 117 to a cathode end $E_1$ of tissue 117) by turning on a first switch $S_1$ of switch array 116 and a third switch $S_3$ of switch array 116. In an exemplary embodiment, during the anodic stimulation, the stimulation current may be passed through the tissue in a positive direction (i.e., from cathode end $E_1$ to anode end $E_2$) by turning off first switch $S_1$ and third switch $S_3$, and turning on a second switch $S_2$ of switch array 116 and a fourth switch $S_4$ of switch array 116. In an exemplary embodiment, switch array 116 may also include a shorting switch $S_{short}$ that may be turned on for a short time after cathodic and anodic stimulations.

In an exemplary embodiment, there may be an interphase delay between cathodic and anodic phases. Therefore, in an exemplary embodiment, first switch $S_1$ and third switch $S_3$ may be kept turned off for a second period of time (i.e., the interphase delay) prior to turning on second switch $S_2$ and fourth switch $S_4$. In an exemplary embodiment, first sampling switch $S_{samp1}$, second sampling switch $S_{samp2}$, and connecting switch $S_{conn}$ may be turned on during the second period of time to put circuit 200 in the sampling phase between the cathodic and anodic phases and remove any mismatch between the currents caused due to the drift of the voltages stored on first holding capacitor $C_{hold1}$ and second holding capacitor $C_{hold2}$ during the cathodic phase. In an exemplary embodiment, first sampling switch $S_{samp1}$, second sampling switch $S_{samp2}$, and connecting switch $S_{conn}$ may be turned off after the second period of time and prior to turning on second switch $S_2$ and fourth switch $S_4$ to enter the anodic phase.

Figure 3:
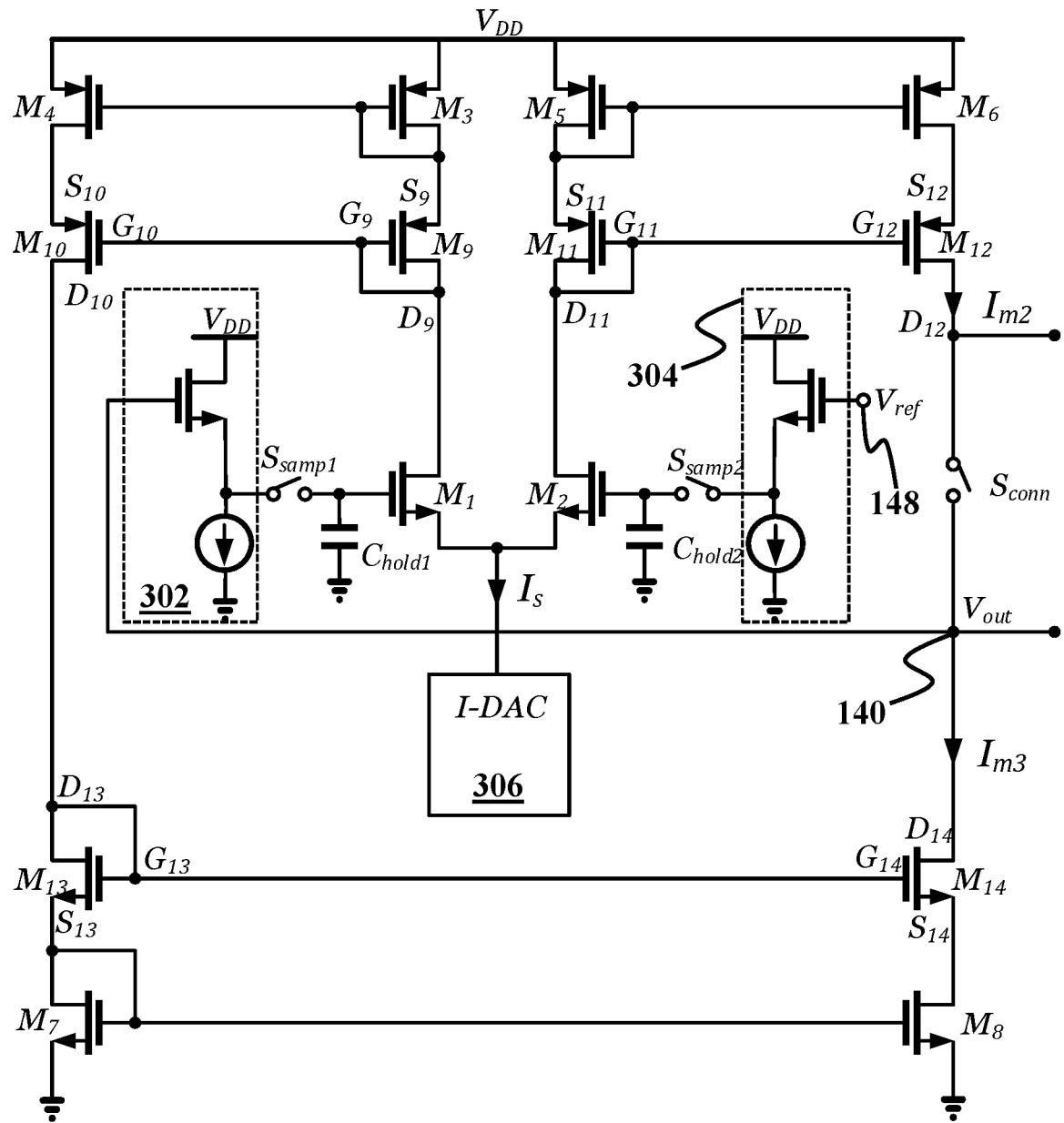
FIG. 3 shows a schematic of a second implementation of a circuit for charge-balanced current-controlled stimulation, consistent with one or more exemplary embodiments of the present disclosure.

FIG. 3 shows a schematic of a second implementation of a circuit for charge-balanced current-controlled stimulation, consistent with one or more exemplary embodiments of the present disclosure. An exemplary circuit 300 may be a second implementation of circuit 100. In an exemplary embodiment, circuit 300 may include additional elements compared to circuit 200.

Referring to FIGS. 2C and 3, in an exemplary embodiment, first current mirror 106A may further include a ninth FET $M_9$ of the second plurality of FETs. In an exemplary embodiment, ninth FET $M_9$ may be connected between first input current node 128 and third drain $D_3$. In an exemplary embodiment, ninth FET $M_9$ may include a ninth source $S_9$, a ninth gate $G_9$, and a ninth drain $D_9$. In an exemplary embodiment, ninth source $S_9$ may be connected to third drain $D_3$. In an exemplary embodiment, ninth gate $G_9$ and ninth drain $D_9$ may be connected to first input current node 128.

In an exemplary embodiment, first current mirror 106A may further include a tenth FET $M_{10}$ of the second plurality of FETs. In an exemplary embodiment, tenth FET $M_{10}$ may be connected between first output current node 130 and fourth drain $D_4$. In an exemplary embodiment, tenth FET $M_{10}$ may include a tenth source $S_{10}$, a tenth gate $G_{10}$, and a tenth drain $D_{10}$. In an exemplary embodiment, tenth source $S_{10}$ may be connected to fourth drain $D_4$. In an exemplary embodiment, tenth gate $G_{10}$ may be connected to ninth gate $G_9$. In an exemplary embodiment, tenth drain $D_{10}$ may be connected to first output current node 130.

Referring to FIGS. 2D and 3, in an exemplary embodiment, second current mirror 108A may further include an eleventh FET $M_{11}$ of the second plurality of FETs. An exemplary eleventh FET $M_{11}$ may be connected between second input current node 134 and fifth drain $D_5$. In an exemplary embodiment, eleventh FET $M_{11}$ may include an eleventh source $S_{11}$, an eleventh gate $G_{11}$, and an eleventh drain $D_{11}$. In an exemplary embodiment, eleventh source $S_{11}$ may be connected to fifth drain $D_5$. In an exemplary embodiment, eleventh gate $G_{11}$ and eleventh drain $D_{11}$ may be connected to second input current node 134.

In an exemplary embodiment, second current mirror 108A may further include a twelfth FET $M_{12}$ of the second plurality of FETs. In an exemplary embodiment, twelfth FET $M_{12}$ may be connected between second output current node 136 and sixth drain $D_6$. In an exemplary embodiment, twelfth FET $M_{12}$ may include a twelfth source $S_{12}$, a twelfth gate $G_{12}$, and a twelfth drain $D_{12}$. In an exemplary embodiment, twelfth source $S_{12}$ may be connected to sixth drain $D_6$. In an exemplary embodiment, twelfth gate $G_{12}$ may be connected to eleventh gate $G_{11}$. In an exemplary embodiment, twelfth drain $D_{12}$ may be connected to second output current node 136.

Referring to FIGS. 2E and 3, in an exemplary embodiment, third current mirror 110A may further include a thirteenth FET $M_{13}$ of the first plurality of FETs. In an exemplary embodiment, thirteenth FET $M_{13}$ may be connected between third input current node 142 and seventh drain $D_7$. In an exemplary embodiment, thirteenth FET $M_{13}$ may include a thirteenth source $S_{13}$, a thirteenth gate $G_{13}$, and a thirteenth drain $D_{13}$. In an exemplary embodiment, thirteenth source $S_{13}$ may be connected to seventh drain $D_7$. In an exemplary embodiment, thirteenth gate $G_{13}$ and thirteenth drain $D_{13}$ may be connected to third input current node 142.

In an exemplary embodiment, third current mirror 110A may further include a fourteenth FET $M_{14}$ of the first plurality of FETs. In an exemplary embodiment, fourteenth FET $M_{14}$ may be connected between third output current node 144 and the eighth drain $D_8$. In an exemplary embodiment, fourteenth FET $M_{14}$ may include a fourteenth source $S_{14}$, a fourteenth gate $G_{14}$, and a fourteenth drain $D_{14}$. In an exemplary embodiment, fourteenth source $S_{14}$ may be connected to eighth drain $D_8$. In an exemplary embodiment, fourteenth gate $G_{14}$ may be connected to thirteenth gate $G_{13}$. In an exemplary embodiment, fourteenth drain $D_{14}$ may be connected to third output current node 144.

Referring to FIGS. 2A and 3, in an exemplary embodiment, circuit 300 may further include a first voltage buffer 302 and a second voltage buffer 304. In an exemplary embodiment, first voltage buffer 302 may be connected between output node 140 node and first sample and hold circuit 112. In an exemplary embodiment, first voltage buffer 302 may be configured to transfer output voltage $V_{out}$ to first sample and hold circuit 112. In an exemplary embodiment, the transferred voltage may be proportional to output voltage $V_{out}$.

In an exemplary embodiment, second voltage buffer 304 may be connected between reference node 148 and second sample and hold circuit 114. In an exemplary embodiment, second voltage buffer 304 may be configured to transfer reference voltage $V_{ref}$ to second sample and hold circuit 114. In an exemplary embodiment, the transferred voltage may be proportional to reference voltage $V_{ref}$.

In an exemplary embodiment, employing voltage buffers may reduce the mismatch between channel charge injection and clock feedthrough effects in first sampling switch $S_{samp1}$ and second sampling switch $S_{samp2}$ when they turn off. Moreover, cascode structures of current mirrors may increase output resistance and current-copying accuracy of the current mirrors. In an exemplary embodiment, current transfer ratios of second current mirror 108A (i.e., scaling ratios of $M_6$ to $M_5$ and $M_{12}$ to $M_{11}$) and third current mirror 110A (i.e., scaling ratios of $M_8$ to $M_7$ and $M_{14}$ to $M_{13}$) may be set to 1:10.

In an exemplary embodiment, current source 104 may include a current digital to analog converter (I-DAC) 306. In an exemplary embodiment, I-DAC 306 may be configured to adjust source current $I_s$ by converting a digital signal to an analog electric current. In an exemplary embodiment, I-DAC 306 may provide different resolutions, which may facilitate determining the amount of stimulation current based on a required stimulation level.

Figure 4:
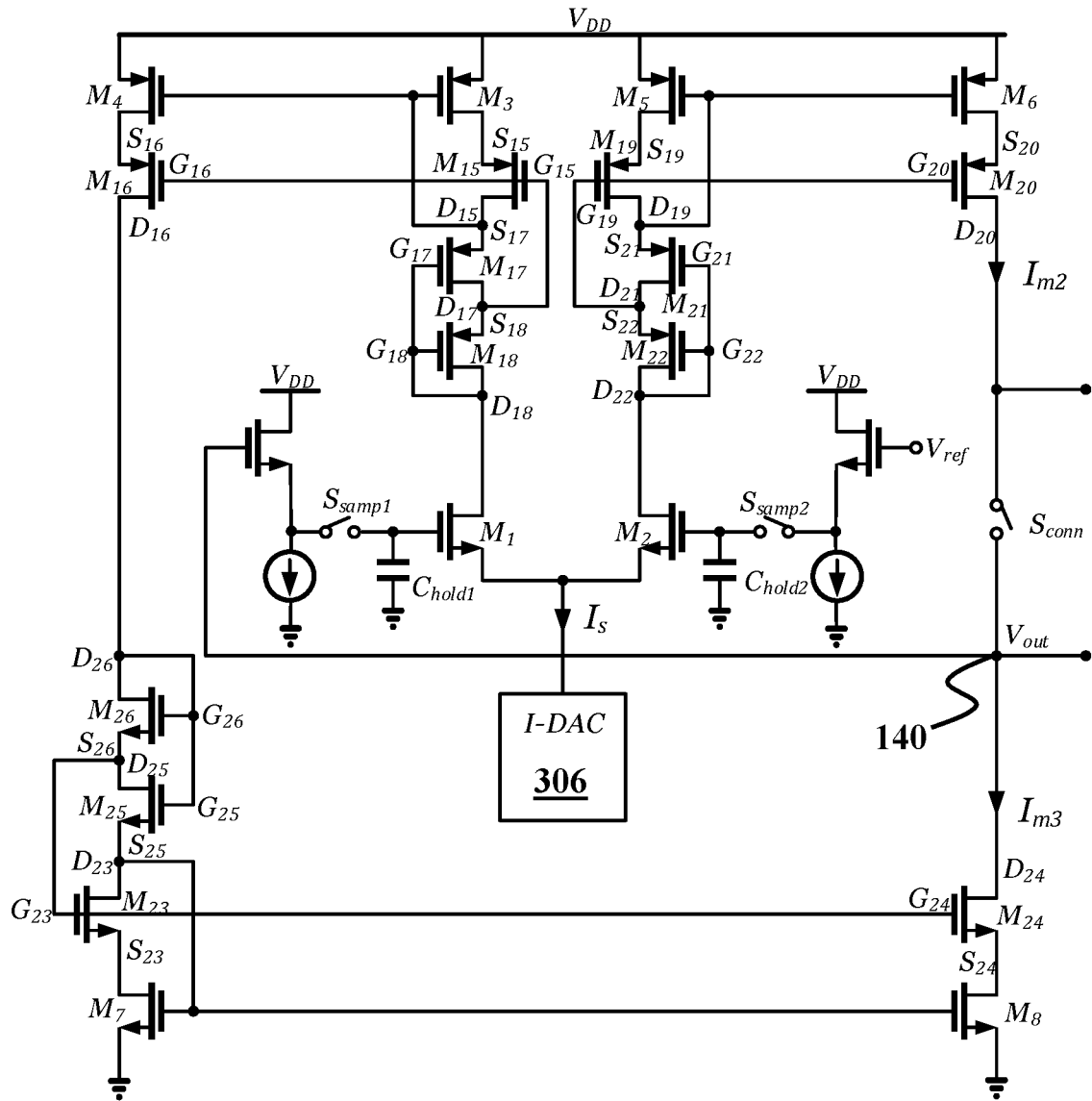
FIG. 4 shows a schematic of a third implementation of a circuit for charge-balanced current-controlled stimulation, consistent with one or more exemplary embodiments of the present disclosure.

FIG. 4 shows a schematic of a third implementation of a circuit for charge-balanced current-controlled stimulation, consistent with one or more exemplary embodiments of the present disclosure. An exemplary circuit 400 may include a third implementation of circuit 100. In an exemplary embodiment, circuit 400 may include additional elements compared to circuit 200.

Referring to FIGS. 2C and 4, in an exemplary embodiment, first current mirror 106A may further include a fifteenth FET $M_{15}$ of the second plurality of FETs connected between first input current node 128 and third drain $D_3$. In an exemplary embodiment, fifteenth FET $M_{15}$ may include a fifteenth source $S_{15}$ connected to third drain $D_3$, a fifteenth gate $G_{15}$, and a fifteenth drain $D_{15}$ connected to third gate $G_3$.

In an exemplary embodiment, first current mirror 106A may further include a sixteenth FET $M_{16}$ of the second plurality of FETs connected between first output current node 130 and fourth drain $D_4$. In an exemplary embodiment, sixteenth FET $M_{16}$ may include a sixteenth source $S_{16}$ connected to fourth drain $D_4$, a sixteenth gate $G_{16}$ connected to fifteenth gate $G_{15}$, and a sixteenth drain $D_{16}$ connected to first output current node 130.

In an exemplary embodiment, first current mirror 106A may further include a seventeenth FET $M_{18}$ of the second plurality of FETs connected between first input current node 128 and fifteenth drain $D_{17}$. In an exemplary embodiment, seventeenth FET $M_{17}$ may include a seventeenth source $S_{17}$ connected to fifteenth drain $D_{15}$, a seventeenth gate $G_{17}$ connected to first input current node 128, and a seventeenth drain $D_{17}$ connected to fifteenth gate $G_{15}$.

In an exemplary embodiment, first current mirror 106A may further include an eighteenth FET $M_{18}$ of the second plurality of FETs connected between first input current node 128 and seventeenth drain $D_{17}$. In an exemplary embodiment, eighteenth FET $M_{18}$ may include an eighteenth source $S_{18}$ connected to seventeenth drain $D_{17}$, an eighteenth gate $G_{18}$ connected to first input current node 128, and an eighteenth drain $D_{18}$ connected to first input current node 128.

Referring to FIGS. 2D and 4, in an exemplary embodiment, second current mirror 108A may further include a nineteenth FET $M_{19}$ of the second plurality of FETs connected between second input current node 134 and fifth drain $D_5$. In an exemplary embodiment, nineteenth FET $M_{19}$ may include a nineteenth source $S_{19}$ connected to fifth drain $D_5$, a nineteenth gate $G_{19}$, and a nineteenth drain $D_{19}$ connected to fifth gate $G_5$.

In an exemplary embodiment, second current mirror 108A may further include a twentieth FET $M_{20}$ of the second plurality of FETs connected between second output current node 136 and sixth drain $D_6$. In an exemplary embodiment, twentieth FET $M_{20}$ may include a twentieth source $S_{20}$ connected to sixth drain $D_6$, a twentieth gate $G_{20}$ connected to nineteenth gate $G_{19}$, and a twentieth drain $D_{20}$ connected to second output current node 136.

In an exemplary embodiment, second current mirror 108A may further include a twenty-first FET $M_{21}$ of the second plurality of FETs connected between second input current node 134 and nineteenth drain $D_{19}$. In an exemplary embodiment, twenty-first FET $M_{21}$ may include a twenty-first source $S_{21}$ connected to nineteenth drain $D_{19}$, a twenty-first gate $G_{21}$ connected to second input current node 134, and a twenty-first drain $D_{21}$ connected to nineteenth gate $G_{19}$.

In an exemplary embodiment, second current mirror 108A may further include a twenty-second FET $M_{22}$ of the second plurality of FETs connected between second input current node 134 and twenty-first drain $D_{21}$. In an exemplary embodiment, twenty-second FET $M_{22}$ may include a twenty-second source $S_{22}$ connected to twenty-first drain $D_{21}$, a twenty-second gate $G_{22}$ connected to second input current node 134, and a twenty-second drain $D_{22}$ connected to second input current node 134.

Referring to FIGS. 2E and 4, in an exemplary embodiment, third current mirror 110A may further include a twenty-third FET $M_{23}$ of the first plurality of FETs connected between third input current node 142 and seventh drain $D_7$. In an exemplary embodiment, twenty-third FET $M_{23}$ may include a twenty-third source $S_{23}$ connected to seventh drain $D_7$, a twenty-third gate $G_{23}$, and a twenty-third drain $D_{23}$ connected to seventh gate $G_7$.

In an exemplary embodiment, third current mirror 110A may further include a twenty-fourth FET $M_{24}$ of the first plurality of FETs connected between third output current node 144 and eighth drain $D_8$. In an exemplary embodiment, twenty-fourth FET $M_{24}$ may include a twenty-fourth source $S_{24}$ connected to eighth drain $D_8$, a twenty-fourth gate $G_{24}$ connected to twenty-third gate $G_{23}$, and a twenty-fourth drain $D_{24}$ connected to third output current node 144.

In an exemplary embodiment, third current mirror 110A may further include a twenty-fifth FET $M_{25}$ of the first plurality of FETs connected between third input current node 142 and twenty-third drain $D_{23}$. In an exemplary embodiment, twenty-fifth FET $M_{25}$ may include a twenty-fifth source $S_{25}$ connected to twenty-third drain $D_{23}$, a twenty-fifth gate $G_{25}$ connected to third input current node 142, and a twenty-fifth drain $D_{25}$ connected to twenty-third gate $G_{23}$.

In an exemplary embodiment, third current mirror 110A may further include a twenty-sixth FET $M_{26}$ of the first plurality of FETs connected between third input current node 142 and twenty-fifth drain $D_{25}$. In an exemplary embodiment, twenty-sixth FET $M_{26}$ may include a twenty-sixth source $S_{26}$ connected to twenty-fifth drain $D_{25}$, a twenty-sixth gate $G_{26}$ connected to third input current node 142, and a twenty-sixth drain $D_{26}$ connected to third input current node 142.

Figure 5:
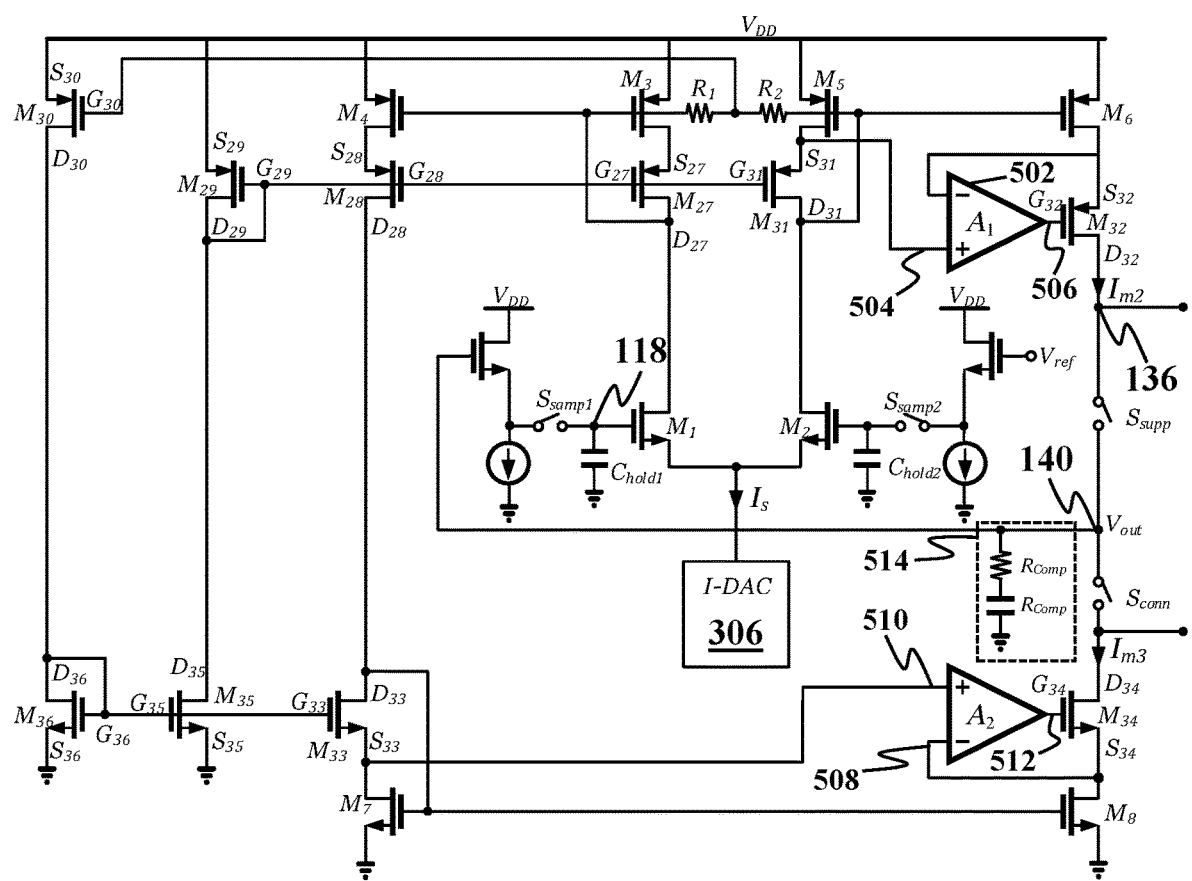
FIG. 5 shows a schematic of a fourth implementation of a circuit for charge-balanced current-controlled stimulation, consistent with one or more exemplary embodiments of the present disclosure.

FIG. 5 shows a schematic of a fourth implementation of a circuit for charge-balanced current-controlled stimulation, consistent with one or more exemplary embodiments of the present disclosure. An exemplary circuit 500 may include a fourth implementation of circuit 100. In an exemplary embodiment, circuit 500 may include additional elements compared to circuit 200.

Referring to FIGS. 2C and 5, in an exemplary embodiment, first current mirror 106A may further include a twenty-seventh FET $M_{27}$ of the second plurality of FETs connected between first input current node 128 and third drain $D_3$. In an exemplary embodiment, twenty-seventh FET $M_{27}$ may include a twenty-seventh source $S_{27}$ connected to third drain $D_3$, a twenty-seventh gate $G_{27}$, and a twenty-seventh drain $D_{27}$ connected to third gate $G_3$.

In an exemplary embodiment, first current mirror 106A may further include a twenty-eighth FET $M_{29}$ of the second plurality of FETs connected between first output current node 130 and fourth drain $D_4$. In an exemplary embodiment, twenty-eighth FET $M_{28}$ may include a twenty-eighth source $S_{28}$ connected to fourth drain $D_4$, a twenty-eighth gate $G_{28}$ connected to twenty-seventh gate $G_{27}$, and a twenty-eighth drain $D_{28}$ connected to first output current node 130.

In an exemplary embodiment, first current mirror 106A may further include a twenty-ninth FET $M_{29}$ of the second plurality of FETs. In an exemplary embodiment, twenty-ninth FET $M_{29}$ may include a twenty-ninth source $S_{29}$ connected to first supply node 132, a twenty-ninth gate $G_{29}$ connected to twenty-eighth gate $G_{28}$, and a twenty-ninth drain $D_{29}$ connected to twenty-ninth gate $G_{29}$.

In an exemplary embodiment, first current mirror 106A may further include a thirtieth FET $M_{30}$ of the second plurality of FETs. In an exemplary embodiment, thirtieth FET $M_5$ may include a thirtieth source $S_{30}$ connected to first supply node 132, a thirtieth gate $G_{30}$ coupled with third gate $G_3$, and a thirtieth drain $D_{30}$. In an exemplary embodiment, first current mirror 106A may further include a first resistor R connected between thirtieth gate $G_{30}$ and the third gate $G_3$.

Referring to FIGS. 2D and 5, in an exemplary embodiment, second current mirror 108A may further include a thirty-first FET $M_{31}$ of the second plurality of FETs connected between second input current node 134 and fifth drain $D_5$. In an exemplary embodiment, thirty-first FET $M_{31}$ may include a thirty-first source $S_{31}$ connected to fifth drain $D_5$, a thirty-first gate $G_{31}$ connected to twenty-seventh gate $G_{27}$ and a thirty-first drain DJ connected to fifth gate $G_5$.

In an exemplary embodiment, second current mirror 108A may further include a thirty-second FET $M_{32}$ of the second plurality of FETs connected between second output current node 136 and sixth drain $D_6$. In an exemplary embodiment, thirty-second FET $M_{32}$ may include a thirty-second source $S_{32}$ connected to sixth drain $D_6$, a thirty-second gate $G_{32}$ coupled with thirty-first gate $G_{31}$, and a thirty-second drain $D_{32}$ connected to second output current node 136. In an exemplary embodiment, second current mirror 108A may further include a second resistor $R_2$ connected between fifth gate $G_5$ and first resistor $R_1$.

Referring to FIGS. 2E and 5, in an exemplary embodiment, third current mirror 110A may further include a thirty-third FET $M_{33}$ of the first plurality of FETs connected between third input current node 142 and seventh drain $D_7$. In an exemplary embodiment, thirty-third FET $M_{33}$ may include a thirty-third source $S_{33}$ connected to seventh drain $D_7$, a thirty-third gate $G_{33}$, and a thirty-third drain $D_{33}$ connected to seventh gate $G_7$.

In an exemplary embodiment, third current mirror 110A may further include a thirty-fourth FET $M_{34}$ of the first plurality of FETs connected between third output current node 144 and eighth drain $D_8$. In an exemplary embodiment, thirty-fourth FET $M_{34}$ may include a thirty-fourth source $S_{34}$ connected to eighth drain $D_8$, a thirty-fourth gate $G_{34}$ coupled with thirty-third gate $G_{33}$, and a thirty-fourth drain $D_{34}$ connected to third output current node 144.

In an exemplary embodiment, third current mirror 110A may further include a thirty-fifth FET $M_{35}$ of the first plurality of FETs. In an exemplary embodiment, thirty-fifth FET $M_{35}$ may include a thirty-fifth source $S_{35}$ connected to third supply node 146, a thirty-fifth gate $G_{35}$ connected to thirty-third gate $G_{33}$, and a thirty-fifth drain $D_{35}$ connected to twenty-ninth drain $D_{29}$.

In an exemplary embodiment, third current mirror 110A may further include a thirty-sixth FET $M_{36}$ of the first plurality of FETs. In an exemplary embodiment, thirty-sixth FET $M_{36}$ may include a thirty-sixth source $S_{36}$ connected to third supply node 146, a thirty-sixth gate $G_{36}$ connected to thirty-fifth gate $G_{35}$, and a thirty-sixth drain $D_{36}$ connected to thirtieth drain $D_{30}$ and thirty-sixth gate $G_{36}$.

In an exemplary embodiment, circuit 500 may further include a first operational amplifier (op-amp) A configured to couple thirty-first FET $M_{31}$ with the thirty-second FET. In an exemplary embodiment, first op-amp $A_1$ may include a first inverting input 502 connected to thirty-second source $S_{32}$, a first non-inverting input 504 connected to thirty-first source $S_{31}$, and a first op-amp output 506 connected to thirty-second gate $G_{32}$.

In an exemplary embodiment, circuit 500 may further include a second op-amp $A_2$ configured to couple thirty-third FET $M_{33}$ with thirty-fourth FET $M_{34}$. In an exemplary embodiment, second op-amp $A_2$ may include a second inverting input 508 connected to thirty-fourth source $S_{34}$, a second non-inverting input 510 connected to thirty-third source $S_{33}$, and a second op-amp output 512 connected to thirty-fourth gate $G_{34}$.

In an exemplary embodiment, first current mirror 106A may further include a first transfer ratio of equal to one, i.e., the scaling ratios of $M_3$ to $M_4$ and $M_{27}$ to $M_{28}$ may be 1:1. In an exemplary embodiment, second current mirror 108A may further include a second transfer ratio equal to four, i.e., the scaling ratios of $M_5$ to $M_6$ and $M_{31}$ to $M_{32}$ may be 1:4. In an exemplary embodiment, third current mirror 110A may further include a third transfer ratio equal to four, i.e., the scaling ratios of $M_7$ to $M_8$ and $M_{33}$ to $M_{34}$ may be 1:4.

In an exemplary embodiment, resistors $R_1$ and $R_2$ may have large values and may generate a common-mode voltage of gates $G_3$ and $G_5$. In an exemplary embodiment, this common-mode voltage may generate a bias voltage of FET $M_{30}$. Therefore, in an exemplary embodiment, the current of FET $M_{30}$ may be approximately equal to the average of the currents of FETs $M_3$ and $M_5$. In an exemplary embodiment, the current of FET $M_{30}$ may bias FET $M_{36}$ which may be a diode-connected transistor that may generate a bias voltage for gates $G_{33}$, $G_{34}$, and $G_{35}$.

In an exemplary embodiment, the current of FET $M_{35}$ may bias FET $M_{29}$, which is may be diode-connected transistor that biases gates $G_{27}$, $G_{28}$, $G_{29}$, and $G_{31}$. In an exemplary embodiment, a bias current in FETs $M_{29}$, $M_{30}$, $M_{35}$, and $M_{36}$ may track source current $I_s$ generated by I-DAC 306. Therefore, in an exemplary embodiment, at low I-DAC currents, voltage levels at gates $G_{27}$ and $G_{31}$ may move up and may help keeping FETs $M_{27}$ and $M_{31}$ in saturation. Similarly, in an exemplary embodiment, voltage levels at gates $G_{33}$ and $G_{34}$ may move down and help keeping FET $M_{33}$ in saturation.

In an exemplary embodiment, circuit 500 circuit may further include a supplementary switch $S_{supp}$ and an RC circuit 514. In an exemplary embodiment, supplementary switch $S_{supp}$ may be connected between second output current node 136 and output node 140. In an exemplary embodiment, supplementary switch $S_{supp}$ may be configured to connect second output current node 136 to output node 140 responsive to supplementary switch $S_{supp}$ turned on. In an exemplary embodiment, RC circuit 514 may be connected between output node 140 and the ground node. In an exemplary embodiment, RC circuit 514 may include a compensating resistor $R_{comp}$ and a compensating capacitor $C_{comp}$ connected in series. In an exemplary embodiment, RC circuit 514 may provide frequency compensation to increase the stability of the feedback loop when the circuit is in sampling phase.

Figure 6:
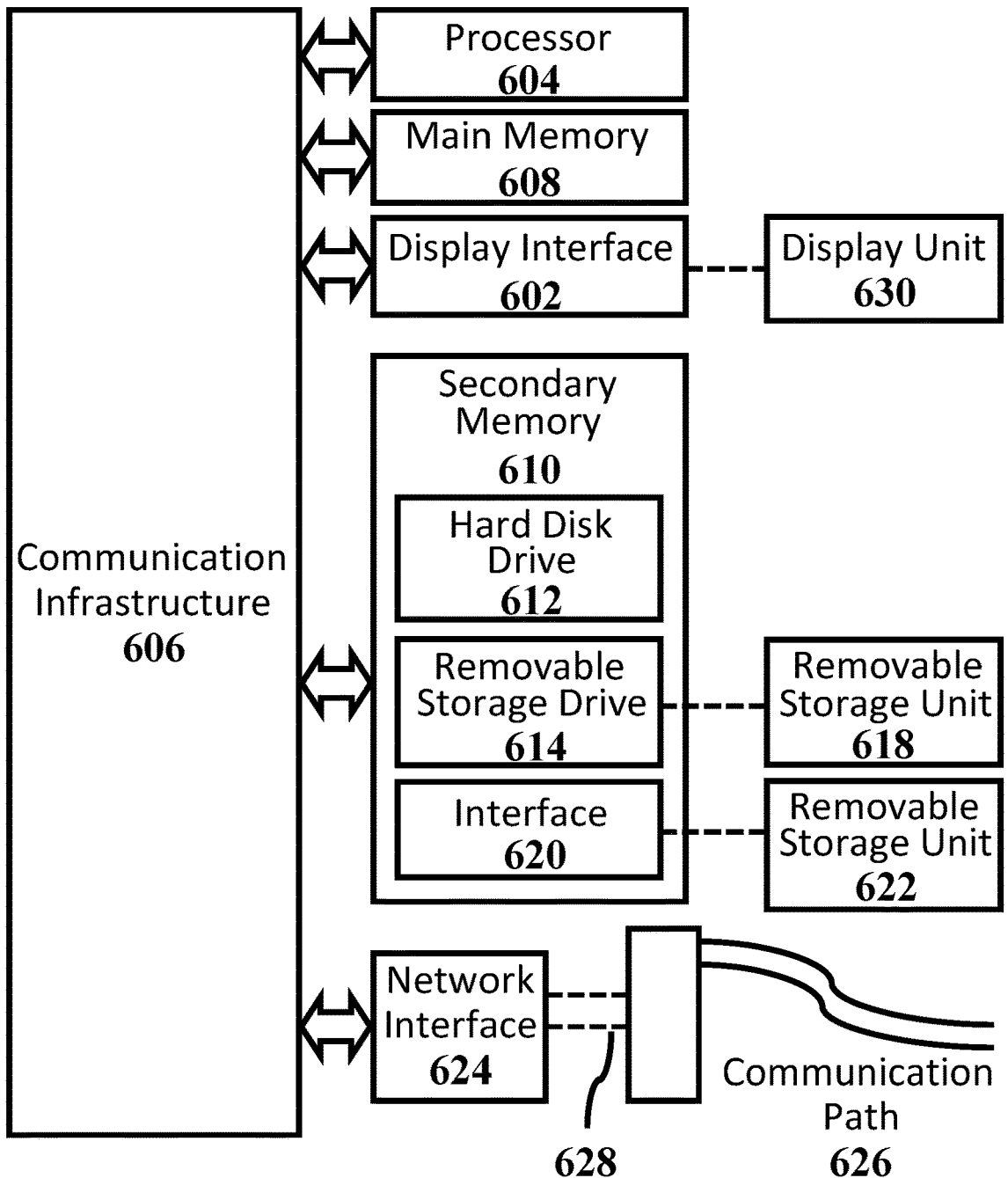
FIG. 6 shows a high-level functional block diagram of a computer system, consistent with one or more exemplary embodiments of the present disclosure.

FIG. 6 shows an example computer system 600 in which an embodiment of the present invention, or portions thereof, may be implemented as computer-readable code, consistent with exemplary embodiments of the present disclosure. For example, first sampling switch $S_{samp1}$, second sampling switch $S_{samp2}$, connecting switch $S_{conn}$, supplementary switch $S_{supp}$, and each switch in switch array 116 may be turned on/off by computer system 600 using hardware, software, firmware, tangible computer readable media having instructions stored thereon, or a combination thereof and may be implemented in one or more computer systems or other processing systems. Hardware, software, or any combination of such may embody any of the units and components in FIGS. 1-5.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 604 may be a special purpose or a general-purpose processor device. As will be appreciated by persons skilled in the relevant art, processor device 604 may also be a single processor in a multi-core/multiprocessor system, such system operating alone, or in a cluster of computing devices operating in a cluster or server farm. Processor device 604 may be connected to a communication infrastructure 606, for example, a bus, message queue, network, or multi-core message-passing scheme.

In an exemplary embodiment, computer system 600 may include a display interface 602, for example a video connector, to transfer data to a display unit 630, for example, a monitor. Computer system 600 may also include a main memory 608, for example, random access memory (RAM), and may also include a secondary memory 610. Secondary memory 610 may include, for example, a hard disk drive 612, and a removable storage drive 614. Removable storage drive 614 may include a floppy disk drive, a magnetic tape drive, an optical disk drive, a flash memory, or the like. Removable storage drive 614 may read from and/or write to a removable storage unit 618 in a well-known manner. Removable storage unit 618 may include a floppy disk, a magnetic tape, an optical disk, etc., which may be read by and written to by removable storage drive 614. As will be appreciated by persons skilled in the relevant art, removable storage unit 618 may include a computer usable storage medium having stored therein computer software and/or data.

In alternative implementations, secondary memory 610 may include other similar means for allowing computer programs or other instructions to be loaded into computer system 600. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 which allow software and data to be transferred from removable storage unit 622 to computer system 600.

Computer system 600 may also include a communications interface 624. Communications interface 624 allows software and data to be transferred between computer system 600 and external devices. Communications interface 624 may include a modem, a network interface (such as an Ethernet card), a communications port, a PCMCIA slot and card, or the like. Software and data transferred via communications interface 624 may be in the form of signals, which may be electronic, electromagnetic, optical, or other signals capable of being received by communications interface 624. These signals may be provided to communications interface 624 via a communications path 626. Communications path 626 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Computer program medium and computer usable medium may also refer to memories, such as main memory 608 and secondary memory 610, which may be memory semiconductors (e.g. DRAMs, etc.).

Computer programs (also called computer control logic) are stored in main memory 508 and/or secondary memory 610. Computer programs may also be received via communications interface 624. Such computer programs, when executed, enable computer system 600 to implement different embodiments of the present disclosure as discussed herein. In particular, the computer programs, when executed, enable processor device 604 to implement the processes of the present disclosure. Accordingly, such computer programs represent controllers of computer system 600. Where an exemplary embodiment in the present disclosure is implemented using software, the software may be stored in a computer program product and loaded into computer system 600 using removable storage drive 614, interface 620, and hard disk drive 612, or communications interface 624.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMs, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

Example

Figure 7:
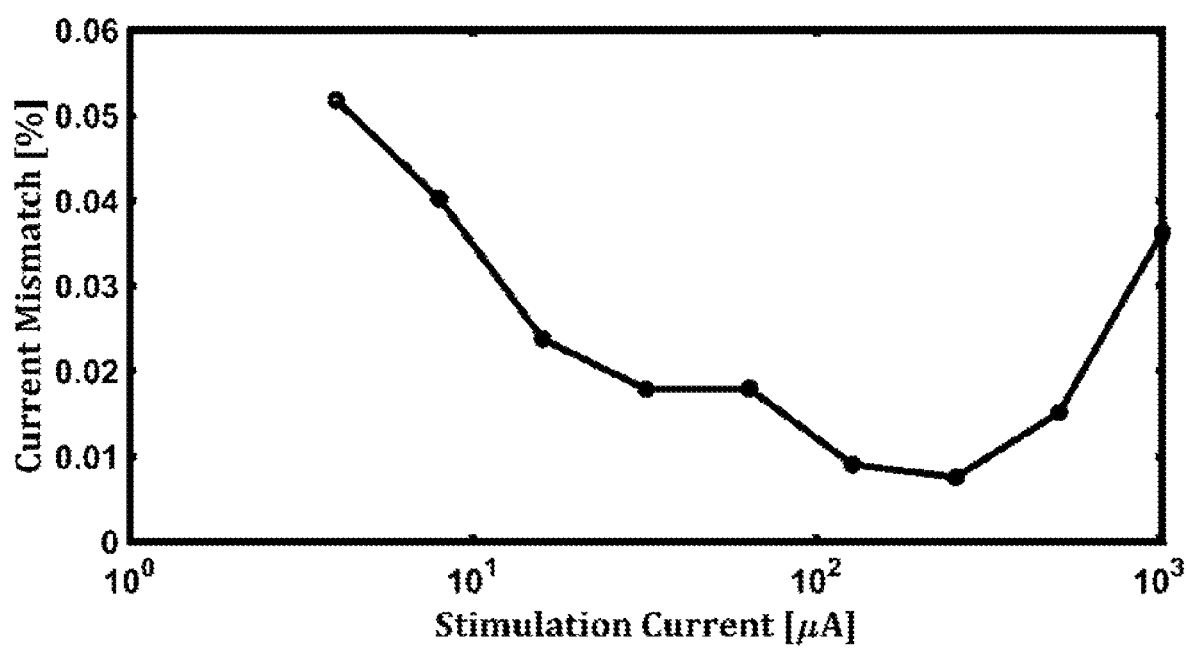
FIG. 7 shows a simulated percent mismatch between anodic and cathodic currents of a current-controlled stimulation circuit, consistent with exemplary embodiments of the present disclosure.

In this example, mismatch between anodic and cathodic currents of a current-controlled stimulation circuit designed based on the configuration shown in FIG. 5 is demonstrated. FIG. 7 shows a simulated percent mismatch between anodic and cathodic currents of a current-controlled stimulation circuit, consistent with exemplary embodiments of the present disclosure. An exemplary circuit is prepared in a 0.18 μm CMOS process and with $V_{DD}$=5V. A simulated 10 mV dc voltage source is placed in series with gate $G_1$ of $M_1$ to deliberately introduce a large mismatch into the circuit. If there is no feedback in the circuit, the 10 mV offset may introduce more than 15% mismatch between second mirrored current $I_{m2}$ and third mirrored current $I_{m3}$. But, utilizing the exemplary circuit, the mismatch is reduced to less than 0.06%. For example, the percent mismatch for a full-scale stimulation current, i.e. 1000 uA, may be less than 0.04%. In other words, the exemplary circuit reduces the mismatch by more than 375 times.

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A circuit for charge-balanced current-controlled stimulation, the circuit comprising:
   a transistor differential pair comprising a first transistor, a second transistor, a first differential input node, a second differential input node, a first differential output node, a second differential output node, and a common node, the transistor differential pair configured to generate a first differential current passing through the first differential output node and a second differential current passing through the second differential output node, a difference between the first differential current and the second differential current proportional to a voltage difference between the first differential input node and the second differential input node;
   a current source configured to generate a source current flowing through the common node;
   a first current mirror comprising a first input current node connected to the first differential output node, a first output current node, and a first supply node coupled with a first supply voltage, the first current mirror configured to generate a first mirrored current flowing through the first output current node based on the first differential current;
   a second current mirror comprising a second input current node connected to the second differential output node, a second output current node coupled with an output node, and a second supply node coupled with the first supply voltage, the second current mirror configured to generate a second mirrored current flowing through the second output current node based on the second differential current;
   a third current mirror comprising a third input current node connected to the first output current node, a third output current node, and a third supply node connected to a second supply voltage, the third current mirror configured to generate a third mirrored current flowing through the third output current node based on the first mirrored current;
   a connecting switch configured to couple the output node with the third output current node responsive to the connecting switch being turned on;
   a first sample and hold circuit comprising a first sampling switch and a first holding capacitor, the first sample and hold circuit configured to:
      sample an output voltage at the output node responsive to the first sampling switch turned on; and
      hold the output voltage at the first differential input node utilizing the first holding capacitor responsive to the first sampling switch turned off; and
   a second sample and hold circuit comprising a second sampling switch and a second holding capacitor, the second sample and hold circuit configured to:
      sample a reference voltage applied to a reference node responsive to the second sampling switch turned on; and
      hold the reference voltage at the second differential input node utilizing the second holding capacitor responsive to the second sampling switch being turned off.

2. The circuit of claim 1, wherein:
   the first transistor comprises a first field effect transistor (FET) of a first plurality of FETs, the first FET comprising:
      a first source connected to the common node;
      a first gate connected to the first differential input node; and a first drain connected to the first differential output node; and the second transistor comprises a second FET of the first plurality of FETs, the second FET comprising:
a second source connected to the common node;
a second gate connected to the second differential input node; and
a second drain connected to the second differential output node.

3. The circuit of claim 2, wherein the first current mirror further comprises:
a third FET of a second plurality of FETs, the third FET comprising:
a third source coupled with the first supply node;
a third gate coupled with the first input current node; and
a third drain coupled with the first input current node; and
a fourth FET of the second plurality of FETs, the fourth FET comprising:
a fourth source coupled with the first supply node;
a fourth gate coupled with the third gate; and
a fourth drain coupled with the first output current node.

4. The circuit of claim 3, wherein the second current mirror further comprises:
a fifth FET of the second plurality of FETs, the fifth FET comprising:
a fifth source coupled with the second supply node;
a fifth gate coupled with the second input current node; and
a fifth drain coupled with the second input current node; and
a sixth FET of the second plurality of FETs, the sixth FET comprising:
a sixth source coupled with the second supply node;
a sixth gate coupled with the fifth gate; and
a sixth drain coupled with the second output current node.

5. The circuit of claim 4, wherein the third current mirror further comprises:
a seventh FET of the first plurality of FETs, the seventh FET comprising:
a seventh source connected to the third supply node;
a seventh gate coupled with the third input current node; and
a seventh drain coupled with the third input current node; and
an eighth FET of the first plurality of FETs, the eighth FET comprising:
an eighth source connected to the third supply node;
an eighth gate connected to the seventh gate; and
an eighth drain coupled with the third output current node.

6. The circuit of claim 5, wherein:
the first current mirror further comprises:
a ninth FET of the second plurality of FETs connected between the first input current node and the third drain, the ninth FET comprising:
a ninth source connected to the third drain;
a ninth gate connected to the first input current node; and
a ninth drain connected to the first input current node; and
a tenth FET of the second plurality of FETs connected between the first output current node and the fourth drain, the tenth FET comprising:
a tenth source connected to the fourth drain;
a tenth gate connected to the ninth gate; and
a tenth drain connected to the first output current node;
the second current mirror further comprises:
an eleventh FET of the second plurality of FETs connected between the second input current node and the fifth drain, the eleventh FET comprising:
an eleventh source connected to the fifth drain;
an eleventh gate connected to the second input current node; and
an eleventh drain connected to the second input current node; and
a twelfth FET of the second plurality of FETs connected between the second output current node and the sixth drain, the twelfth FET comprising:
a twelfth source connected to the sixth drain;
a twelfth gate connected to the eleventh gate; and
a twelfth drain connected to the second output current node; and
the third current mirror further comprises:
a thirteenth FET of the first plurality of FETs connected between the third input current node and the seventh drain, the thirteenth FET comprising:
a thirteenth source connected to the seventh drain;
a thirteenth gate connected to the third input current node; and
a thirteenth drain connected to the third input current node; and
a fourteenth FET of the first plurality of FETs connected between the third output current node and the eighth drain, the fourteenth FET comprising:
a fourteenth source connected to the eighth drain;
a fourteenth gate connected to the thirteenth gate; and
a fourteenth drain connected to the third output current node.

7. The circuit of claim 5, wherein:
the first current mirror further comprises:
a fifteenth FET of the second plurality of FETs connected between the first input current node and the third drain, the fifteenth FET comprising:
a fifteenth source connected to the third drain;
a fifteenth gate; and
a fifteenth drain connected to the third gate;
a sixteenth FET of the second plurality of FETs connected between the first output current node and the fourth drain, the sixteenth FET comprising:
a sixteenth source connected to the fourth drain;
a sixteenth gate connected to the fifteenth gate; and
a sixteenth drain connected to the first output current node;
a seventeenth FET of the second plurality of FETs connected between the first input current node and the fifteenth drain, the seventeenth FET comprising:
a seventeenth source connected to the fifteenth drain;
a seventeenth gate connected to the first input current node; and
a seventeenth drain connected to the fifteenth gate; and
an eighteenth FET of the second plurality of FETs connected between the first input current node and the seventeenth drain, the eighteenth FET comprising:
an eighteenth source connected to the seventeenth drain;

an eighteenth gate connected to the first input current node; and an eighteenth drain connected to the first input current node;

the second current mirror further comprises:

a nineteenth FET of the second plurality of FETs connected between the second input current node and the fifth drain, the nineteenth FET comprising:
a nineteenth source connected to the fifth drain;
a nineteenth gate; and
a nineteenth drain connected to the fifth gate;

a twentieth FET of the second plurality of FETs connected between the second output current node and the sixth drain, the twentieth FET comprising:
a twentieth source connected to the sixth drain;
a twentieth gate connected to the nineteenth gate; and
a twentieth drain connected to the second output current node;

a twenty-first FET of the second plurality of FETs connected between the second input current node and the nineteenth drain, the twenty-first FET comprising:
a twenty-first source connected to the nineteenth drain;
a twenty-first gate connected to the second input current node; and
a twenty-first drain connected to the nineteenth gate; and a twenty-second FET of the second plurality of FETs connected between the second input current node and the twenty-first drain, the twenty-second FET comprising:
a twenty-second source connected to the twenty-first drain;
a twenty-second gate connected to the second input current node; and
a twenty-second drain connected to the second input current node; and the third current mirror further comprises:

a twenty-third FET of the first plurality of FETs connected between the third input current node and the seventh drain, the twenty-third FET comprising:
a twenty-third source connected to the seventh drain;
a twenty-third gate; and
a twenty-third drain connected to the seventh gate;

a twenty-fourth FET of the first plurality of FETs connected between the third output current node and the eighth drain, the twenty-fourth FET comprising:
a twenty-fourth source connected to the eighth drain;
a twenty-fourth gate connected to the twenty-third gate; and
a twenty-fourth drain connected to the third output current node;

a twenty-fifth FET of the first plurality of FETs connected between the third input current node and the twenty-third drain, the twenty-fifth FET comprising:
a twenty-fifth source connected to the twenty-third drain;
a twenty-fifth gate connected to the third input current node; and
a twenty-fifth drain connected to the twenty-third gate; and a twenty-sixth FET of the first plurality of FETs connected between the third input current node and the twenty-fifth drain, the twenty-sixth FET comprising:

a twenty-sixth source connected to the twenty-fifth drain;
a twenty-sixth gate connected to the third input current node; and
a twenty-sixth drain connected to the third input current node.

8. The circuit of claim 5, wherein:

the first current mirror further comprises:

a twenty-seventh FET of the second plurality of FETs connected between the first input current node and the third drain, the twenty-seventh FET comprising:
a twenty-seventh source connected to the third drain;
a twenty-seventh gate; and
a twenty-seventh drain connected to the third gate;

a twenty-eighth FET of the second plurality of FETs connected between the first output current node and the fourth drain, the twenty-eighth FET comprising:
a twenty-eighth source connected to the fourth drain;
a twenty-eighth gate connected to the twenty-seventh gate; and
a twenty-eighth drain connected to the first output current node;

a twenty-ninth FET of the second plurality of FETs, comprising:
a twenty-ninth source connected to the first supply node;
a twenty-ninth gate connected to the twenty-eighth gate; and
a twenty-ninth drain connected to the twenty-ninth gate;

a thirtieth FET of the second plurality of FETs, comprising:
a thirtieth source connected to the first supply node;
a thirtieth gate coupled with the third gate; and
a thirtieth drain; and a first resistor connected between the thirtieth gate and the third gate;

the second current mirror further comprises:

a thirty-first FET of the second plurality of FETs connected between the second input current node and the fifth drain, the thirty-first FET comprising:
a thirty-first source connected to the fifth drain;
a thirty-first gate connected to the twenty-seventh gate; and
a thirty-first drain connected to the fifth gate;

a thirty-second FET of the second plurality of FETs connected between the second output current node and the sixth drain, the thirty-second FET comprising:
a thirty-second source connected to the sixth drain;
a thirty-second gate coupled with the thirty-first gate; and
a thirty-second drain connected to the second output current node; and a second resistor connected between the fifth gate and the first resistor; and the third current mirror further comprises:

a thirty-third FET of the first plurality of FETs connected between the third input current node and the seventh drain, the thirty-third FET comprising:
a thirty-third source connected to the seventh drain;
a thirty-third gate; and
a thirty-third drain connected to the seventh gate;

a thirty-fourth FET of the first plurality of FETs connected between the third output current node and the eighth drain, the thirty-fourth FET comprising:

a thirty-fourth source connected to the eighth drain;
a thirty-fourth gate coupled with the thirty-third gate; and
a thirty-fourth drain connected to the third output current node;
a thirty-fifth FET of the first plurality of FETs, comprising:
a thirty-fifth source connected to the third supply node;
a thirty-fifth gate connected to the thirty-third gate; and
a thirty-fifth drain connected to the twenty-ninth drain; and
a thirty-sixth FET of the first plurality of FETs, comprising:
a thirty-sixth source connected to the third supply node;
a thirty-sixth gate connected to the thirty-fifth gate; and
a thirty-sixth drain connected to the thirtieth drain and the thirty-sixth gate.

9. The circuit of claim 8, further comprising:
a first operational amplifier (op-amp) configured to couple the thirty-first FET with the thirty-second FET, the first op-amp comprising:
a first inverting input connected to the thirty-second source;
a first non-inverting input connected to the thirty-first source; and
a first op-amp output connected to the thirty-second gate;
a second op-amp configured to couple the thirty-third FET with the thirty-fourth FET, the second op-amp comprising:
a second inverting input connected to the thirty-fourth source;
a second non-inverting input connected to the thirty-third source; and
a second op-amp output connected to the thirty-fourth gate;
a supplementary switch connected between the second output current node and the output node, the supplementary switch configured to connect the second output current node to the output node responsive to the supplementary switch turned on; and
an RC circuit connected between the output node and the ground node, the RC circuit comprising a compensating resistor and a compensating capacitor connected in series.

10. The circuit of claim 8, wherein:
the first current mirror further comprises a first transfer ratio equal to one;
the second current mirror further comprises a second transfer ratio equal to four; and
the third current mirror further comprises a third transfer ratio equal to four.

11. The circuit of claim 5, wherein each of the first plurality of FETs comprises a first type of FETs and each of the second plurality of FETs comprises a second type of FETs different from the first type, each of the first type and the second type comprising alternatively one of n-channel FETs or a p-channel FETs.

12. The circuit of claim 1, wherein the current source comprises a current digital to analog converter (I-DAC) configured to adjust the source current by converting a digital signal to an analog electric current.

13. The circuit of claim 1, wherein:
the first holding capacitor is connected between the first differential input node and a ground node;
the first sampling switch is connected between the first differential input node and the output node;
the second holding capacitor is connected between the second differential input node and the ground node; and
the second sampling switch is connected between the second differential input node and the reference node.

14. The circuit of claim 1, further comprising:
a first voltage buffer connected between the first output current node and the first sample and hold circuit, the first voltage buffer configured to transfer the output voltage to the first sample and hold circuit; and
a second voltage buffer connected between the reference node and the second sample and hold circuit, the voltage buffer configured to transfer the reference voltage to the second sample and hold circuit.

15. The circuit of claim 1, wherein:
the transistor differential pair comprises one of a cascode differential pair or a gain-boosted cascode differential pair; and
each of the first current mirror, the second current mirror, and the third current mirror comprises one of a cascode current mirror, a regulated cascode current mirror, an enhanced output impedance current mirror, a source-degenerated current mirror, a Widlar current mirror, or a Wilson current mirror.

16. A method for charge-balanced current-controlled stimulation of a tissue, the method comprising:
generating a stimulation current, comprising:
generating a source current flowing through a common node of a transistor differential pair by coupling a current source to the common node;
generating a first differential current passing through a first differential output node of the transistor differential pair and a second differential current passing through a second differential output node of the transistor differential pair by applying a differential voltage between a first differential input node of the transistor differential pair and a second differential input node of the transistor differential pair, a difference between the first differential current and the second differential current proportional to the differential voltage;
generating a first mirrored current passing through a first output current node of a first current mirror based on the first differential current by connecting a first input current node of the first current mirror to the first differential output node;
generating a second mirrored current passing through a second output current node of a second current mirror based on the second differential current, the second output current node coupled with an output node, generating the second mirrored current comprising connecting a second input current node of the second current mirror to the second differential output node;
generating a third mirrored current passing through a third output current node of a third current mirror based on the first mirrored current by connecting a third input current node of the third current mirror to the first output current node;
sampling an output voltage at the output node by turning on a first sampling switch of a first sample and hold circuit utilizing one or more processors, the first sampling switch connected between the first differential input node and the output node;

applying a reference voltage to a reference node;
sampling the reference voltage by turning on a second sampling switch of a second sample and hold circuit utilizing the one or more processors, the second sampling switch connected between the second differential input node and the reference node; and
obtaining the stimulation current by turning on a connecting switch connected between the output node and the third output current node; and
stimulating the tissue by:
holding the output voltage at the first differential input node utilizing a first holding capacitor of the first sample and hold circuit by turning off the first sampling switch utilizing the one or more processors;
holding the reference voltage at the second differential input node utilizing a second holding capacitor of the second sample and hold circuit by turning off the second sampling switch utilizing the one or more processors; and
passing the stimulation current through the tissue by turning off the connecting switch after turning off the first sampling switch and turning off the second sampling switch utilizing the one or more processors.

17. The method of claim 16, wherein turning on the first sampling switch, turning on the second sampling switch, and turning on the connecting switch comprise keeping each of the first sampling switch, the second sampling switch, and the connecting switch turned on fir a first period of time determined based on a capacitance of the first holding capacitor and a capacitance of the second holding capacitor.

18. The method of claim 16, wherein passing the stimulation current through the tissue comprises:
applying a cathodic stimulation on the tissue by passing the stimulation current in a negative direction through the tissue, comprising:
turning on a first switch of a switch array, the first switch connected between the second output current node and an anode end of the tissue; and
turning on a third switch of the switch array, the third switch connected between the third output current node and a cathode end of the tissue; and
applying an anodic stimulation on the tissue by passing the stimulation current in a positive direction through the tissue, comprising:
turning off the first switch and the third switch;
turning on a second switch of the switch array, the second switch connected between the second output current node and the anode end of the tissue; and
turning on a fourth switch of the switch array, the fourth switch connected between the third output current node and the cathode end of the tissue.

19. The method of claim 18, further comprising:
keeping the first switch and the third switch turned off for a second period of time prior to turning on the second switch and the fourth switch;
utilizing the one or more processors, turning on the first sampling switch, the second sampling switch, and the connecting switch during the second period of time; and
utilizing the one or more processors, turning off the first sampling switch, the second sampling switch, and the connecting switch after the second period of time and prior to turning on the second switch and the fourth switch.

20. The method of claim 16, wherein generating the source current comprises adjusting the source current by converting a digital signal to an analog electric current utilizing a current digital to analog converter (I-DAC).

* * * * *